(12) United States Patent
Chang et al.

(10) Patent No.: US 12,098,147 B2
(45) Date of Patent: Sep. 24, 2024

(54) COMPOUND HAVING NOVEL STRUCTURE, COMPLEX COMPRISING SAME, ANTI-CANCER PHARMACEUTICAL COMPOSITION, AND ANTI-CANCER DRUG

(71) Applicant: ETNOVA THERAPEUTICS CORP., Seongnam-si (KR)

(72) Inventors: Yong Min Chang, Daegu (KR); Yeoun Hee Kim, Daegu (KR); Sha Joung Chang, Seongnam-si (KR); Md Kamrul Islam, Daegu (KR)

(73) Assignee: ETNOVA THERAPEUTICS CORP., Gyeonggi-do (KR)

( * ) Notice: Subject to any disclaimer, the term of this patent is extended or adjusted under 35 U.S.C. 154(b) by 778 days.

(21) Appl. No.: 17/052,050

(22) PCT Filed: May 9, 2019

(86) PCT No.: PCT/KR2019/005531
§ 371 (c)(1),
(2) Date: Oct. 30, 2020

(87) PCT Pub. No.: WO2019/216653
PCT Pub. Date: Nov. 14, 2019

(65) Prior Publication Data
US 2022/0024911 A1  Jan. 27, 2022

(30) Foreign Application Priority Data

May 10, 2018 (KR) .................. 10-2018-0053674
May 8, 2019 (KR) .................. 10-2019-0053919

(51) Int. Cl.
*C07D 417/14*   (2006.01)
*A61P 35/00*    (2006.01)
*C07F 15/00*    (2006.01)

(52) U.S. Cl.
CPC ............ *C07D 417/14* (2013.01); *A61P 35/00* (2018.01); *C07F 15/0093* (2013.01)

(58) Field of Classification Search
CPC .................. C07D 417/14; A61P 35/00
See application file for complete search history.

(56) References Cited

U.S. PATENT DOCUMENTS 8,299,285 B2   10/2012  Dilworth et al.

FOREIGN PATENT DOCUMENTS

| KR | 10-1836463 | 3/2018 |
| KR | 10-2018-0055135 | 5/2018 |
| WO | WO 2019/216653 | 11/2019 |

OTHER PUBLICATIONS

Islam et al. J. Med. Chem. 2017, 60, 2993-3001. (Year: 2017).*
Islam et al. (2017, Oct. 18-20). Synthesis and biological evaluation of benzothiazole aniline (BTA) derivatives and their platinum complexes as antitumor agents [Poster Presentation]. 120th Korean Chemical Society Academic Presentation General Assembly and Equipment Exhibition, Korea. (Year: 2017).*
Written Opinion of the International Searching Authority, issued in PCT/KR2019/005531, dated Aug. 6, 2019 (Year: 2019).*
International Search Report and Written Opinion Issued in Corresponding PCT Patent Application No. PCT/KR2019/005531, dated Aug. 6, 2019.
Islam, et al., "Manganese Complex of Ethylenediaminetetraacetic Acid (EDTA)-Benzothiazole Aniline (BTA) Conjugate as a Potential Liver-Targeting MRI Contrast Agent," *Journal of Medicinal Chemistry*, 60: 2993-3001, 2017.
Keri, et al., "A Comprehensive Review in Current Developments of Benzothiazole-Based Molecules in Medicinal Chemistry," *European Journal of Medicinal Chemistry*, 89: 207-251, 2015.

* cited by examiner

*Primary Examiner* — Amanda L. Aguirre
(74) *Attorney, Agent, or Firm* — NORTON ROSE FULBRIGHT US LLP

(57) ABSTRACT

Disclosed is a compound, a complex comprising same, an anti-cancer pharmaceutical composition, and an anti-cancer drug. The compound can have the structure represented by chemical formula 1.

19 Claims, 15 Drawing Sheets

[FIG. 1a]
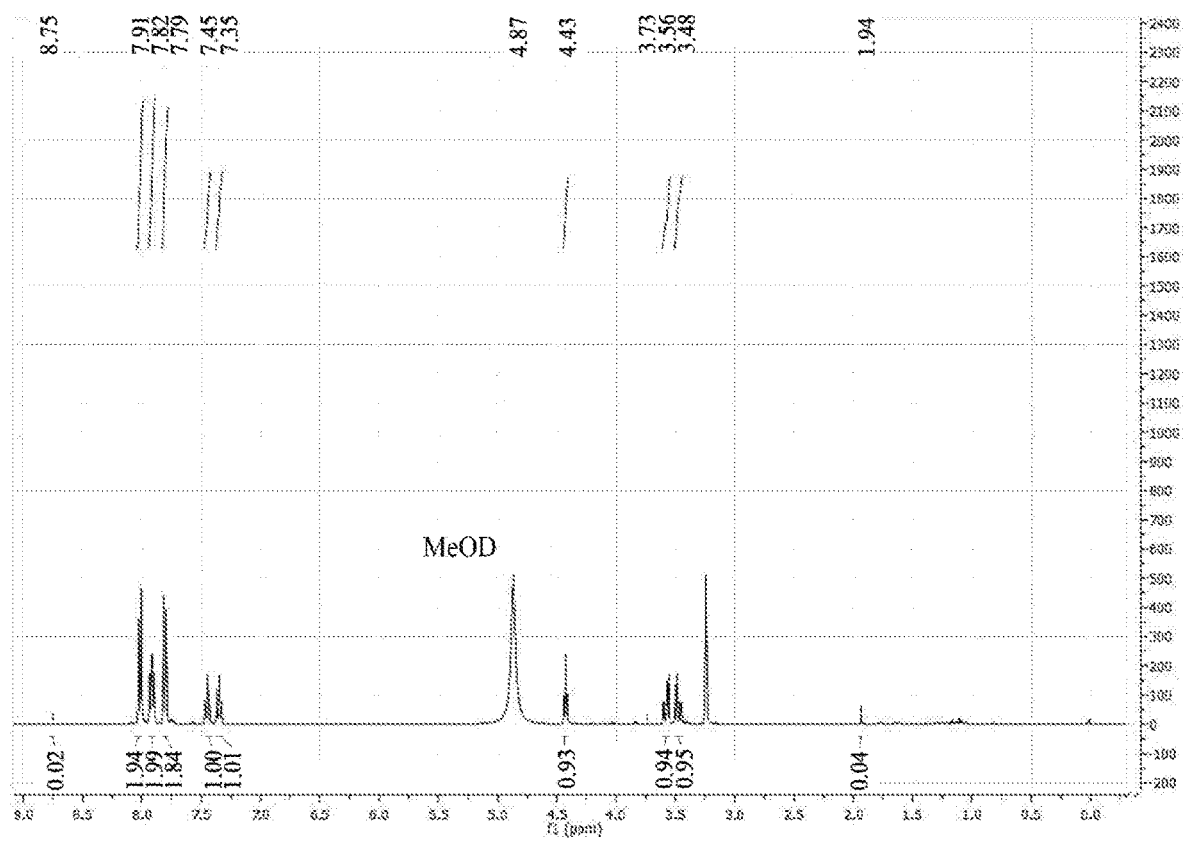

[FIG. 1b]
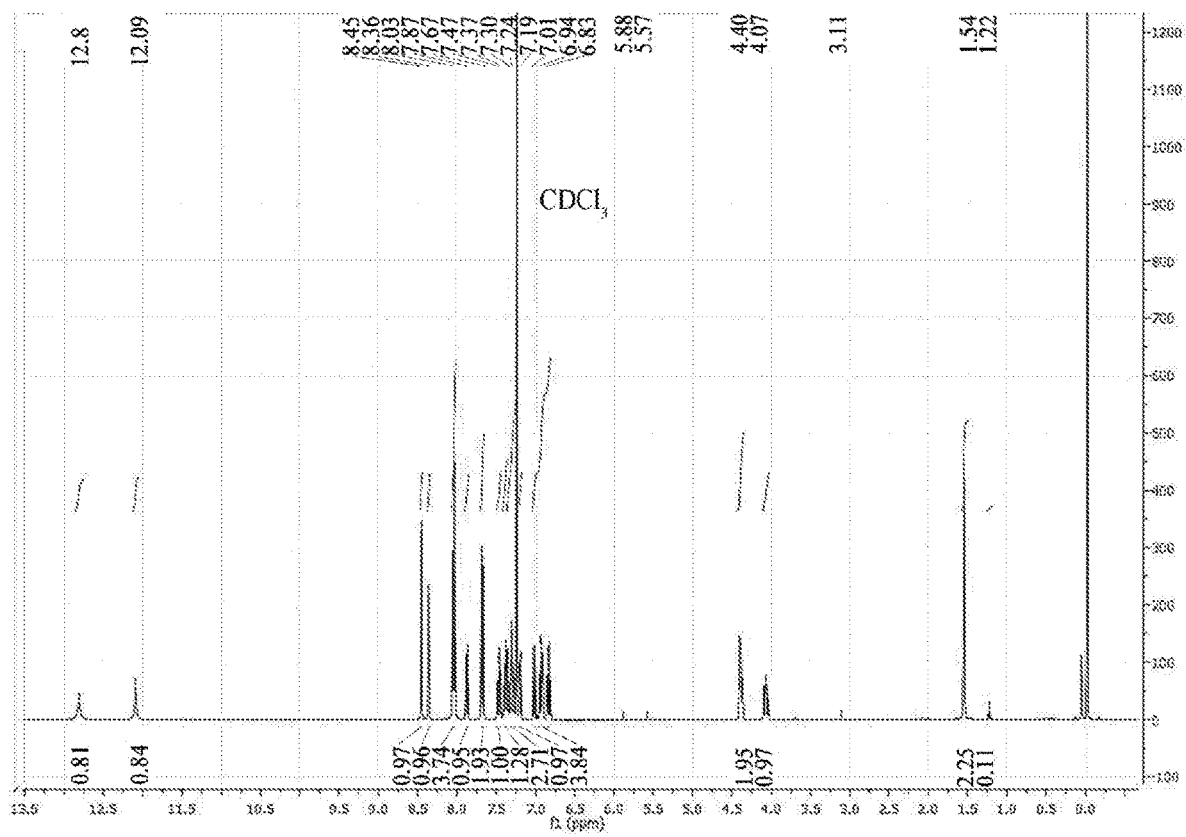

[FIG. 1c]
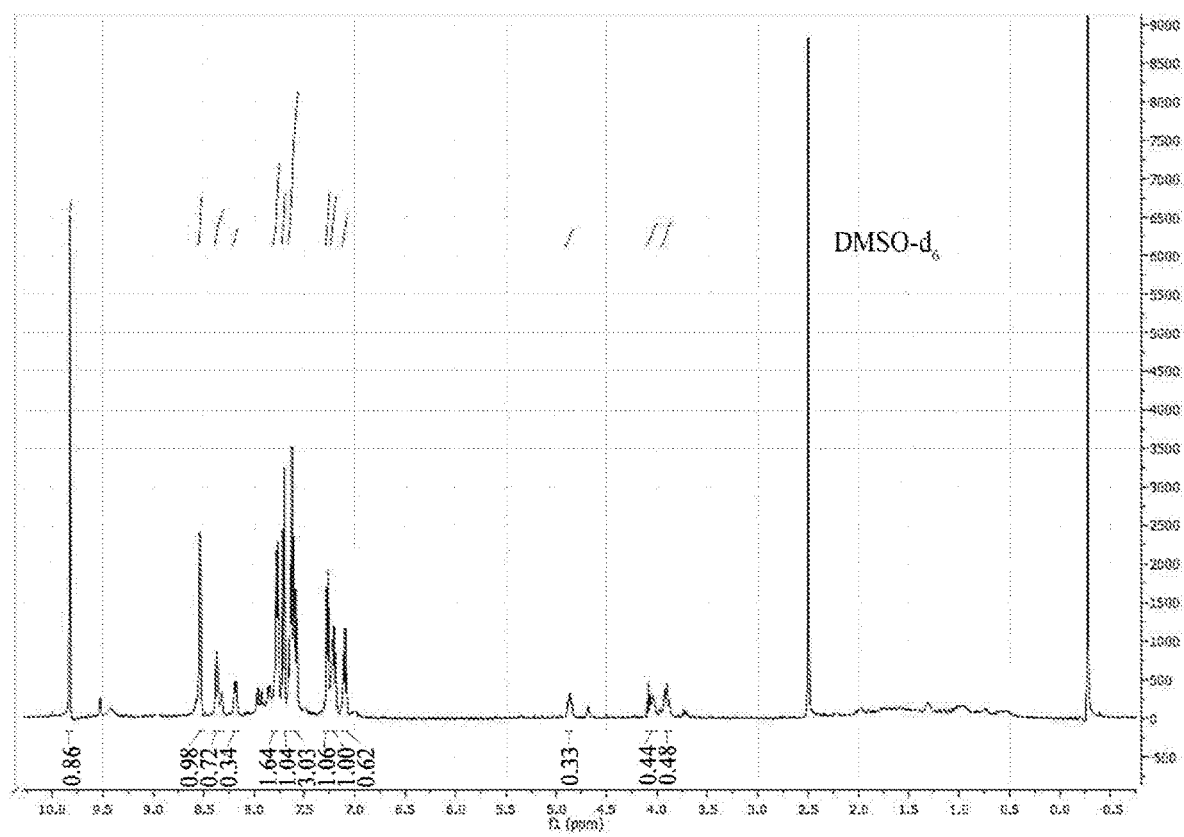

[FIG. 1d]
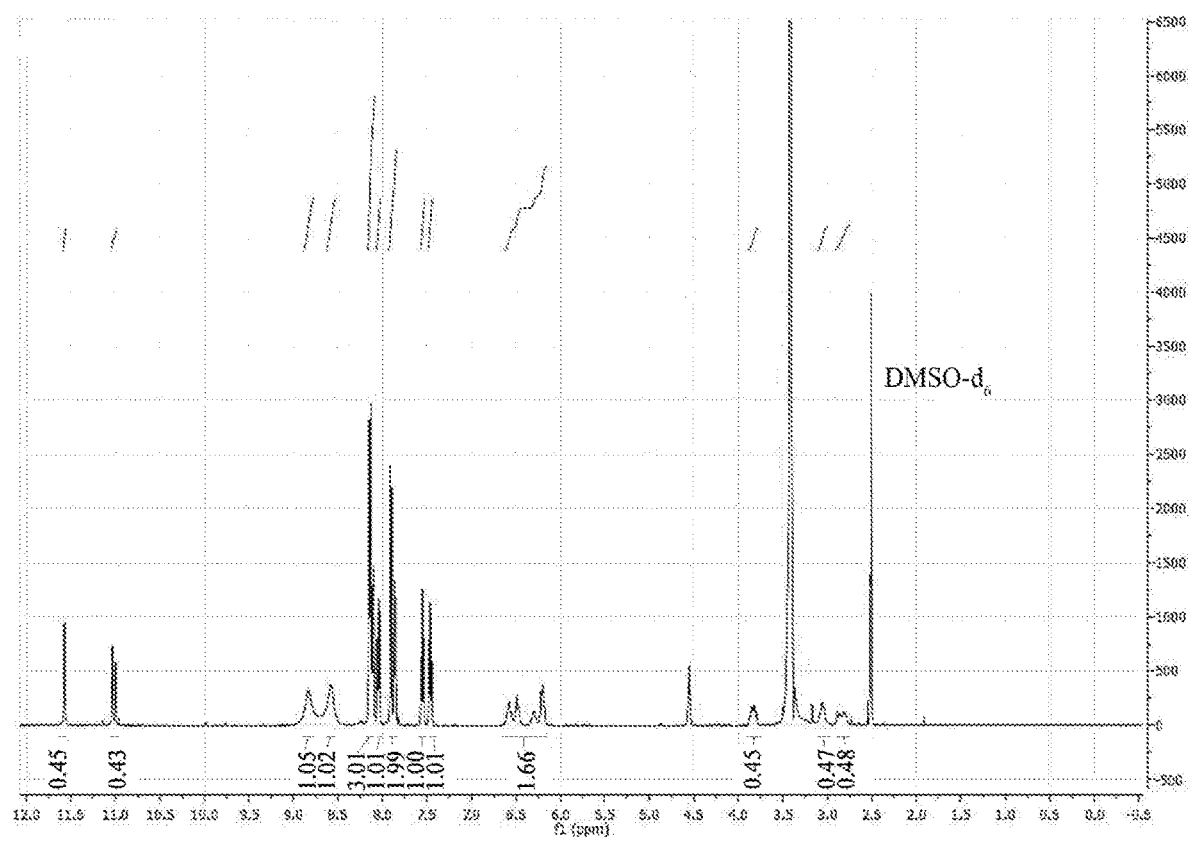

[FIG. 1e]
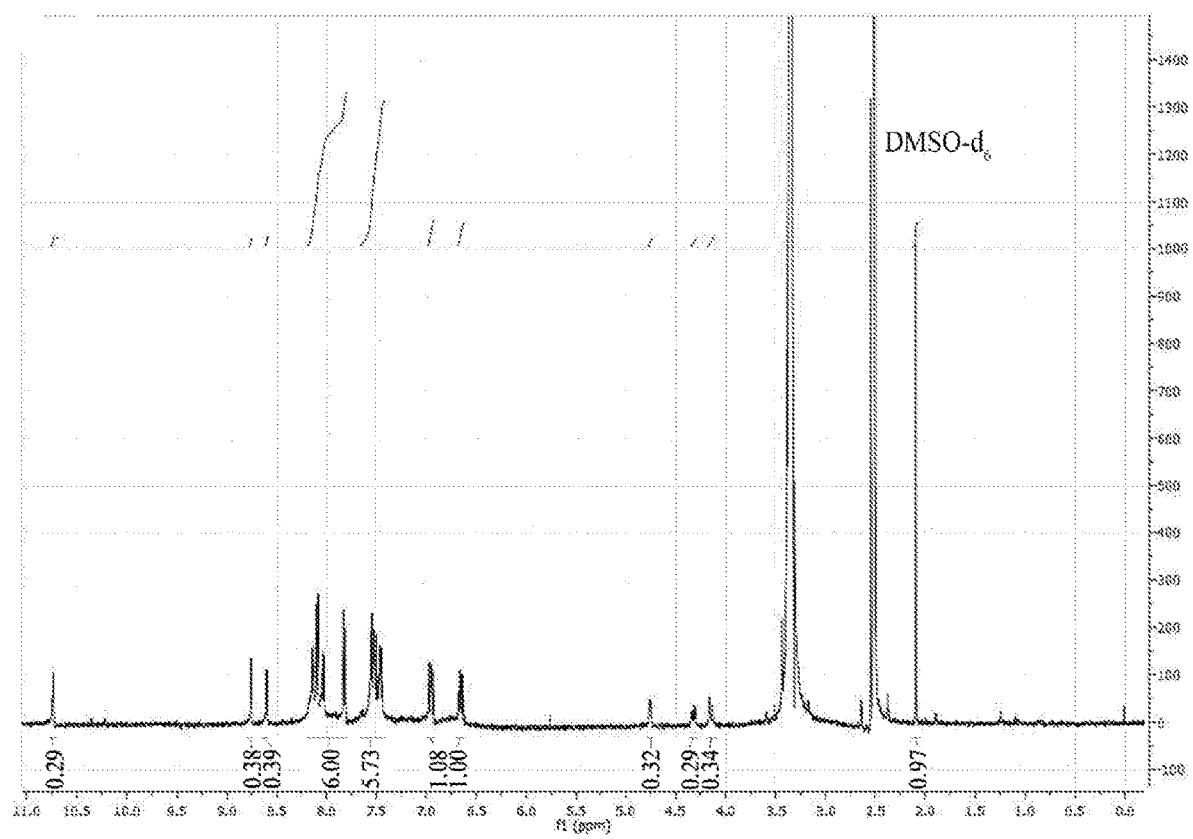

[FIG. 1f]
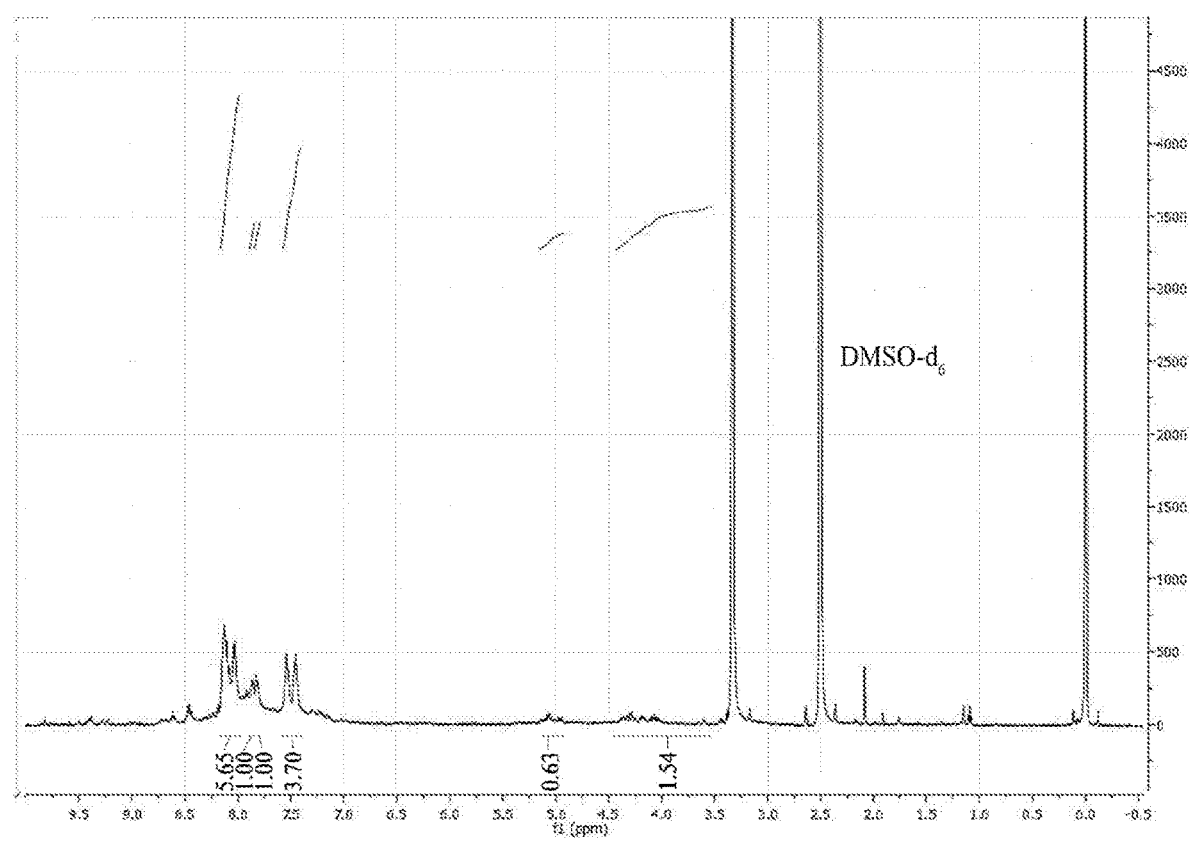

【FIG. 2a】
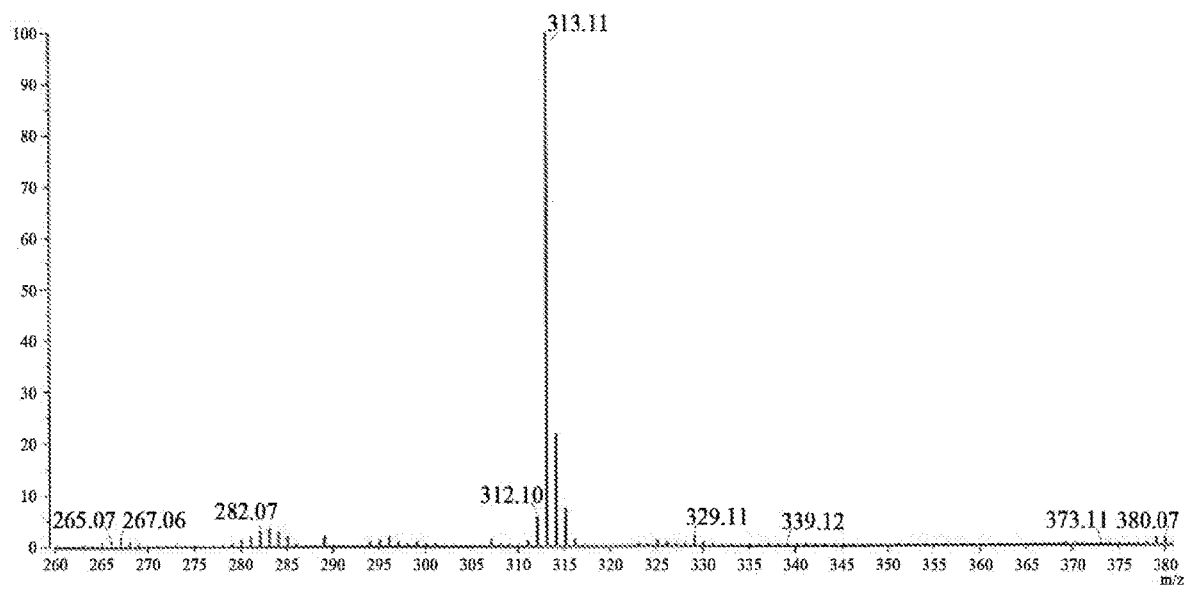
【FIG. 2b】
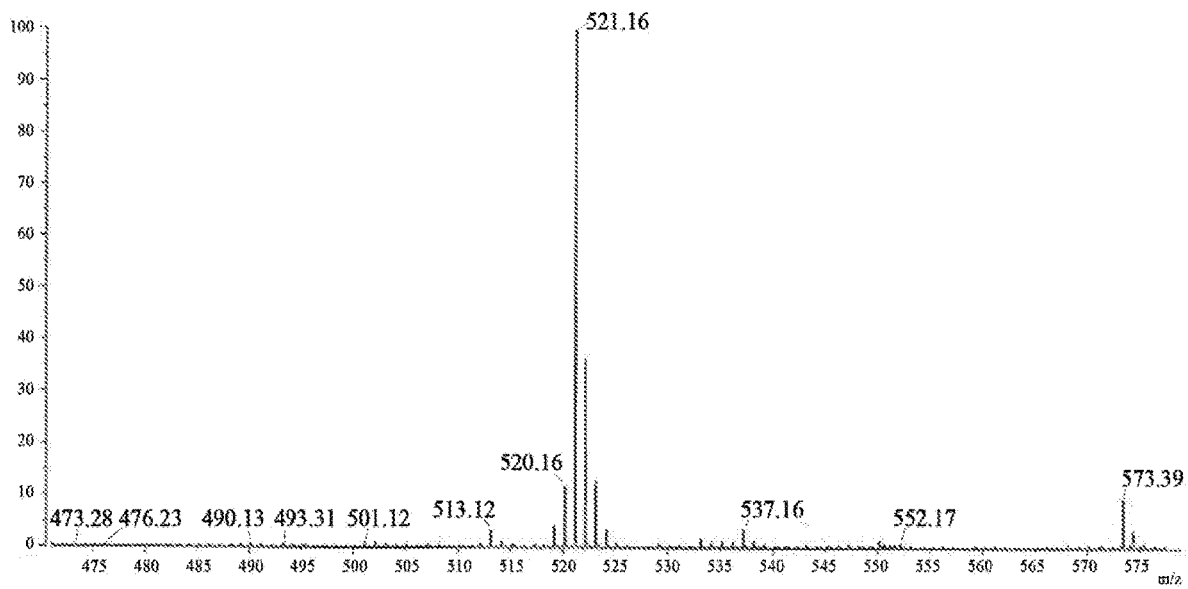

【FIG. 2c】
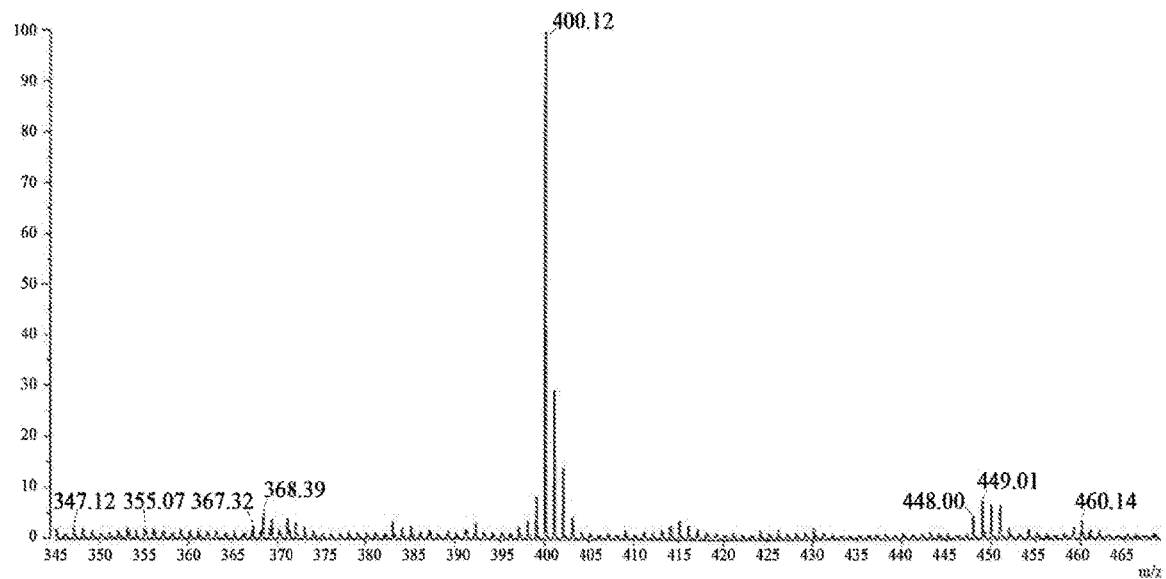
【FIG. 2d】
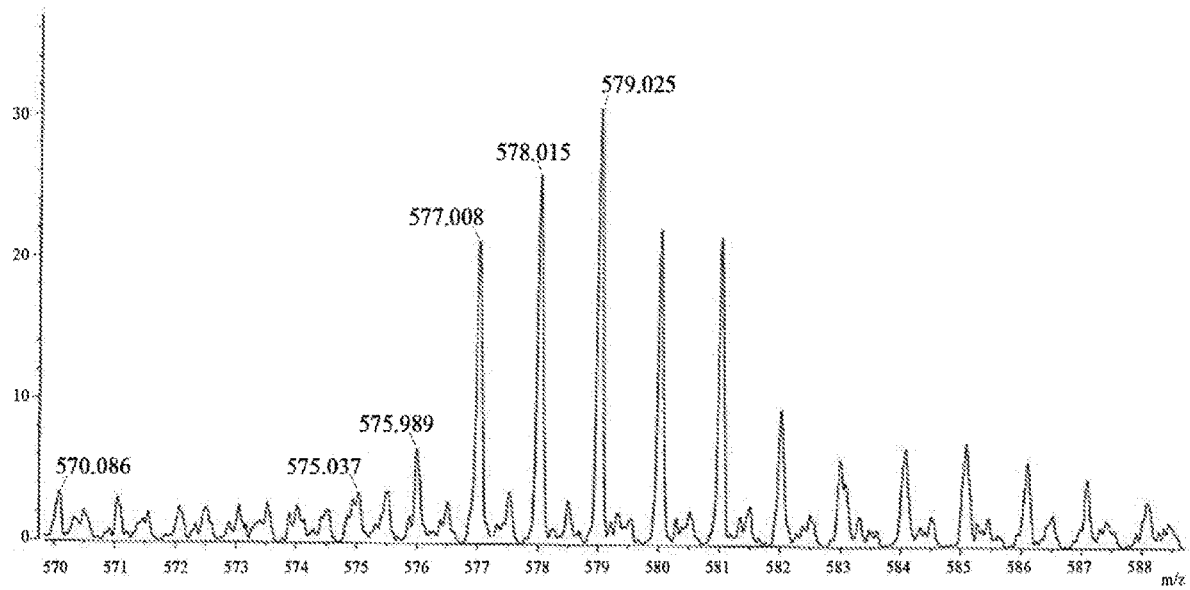

【FIG. 2e】
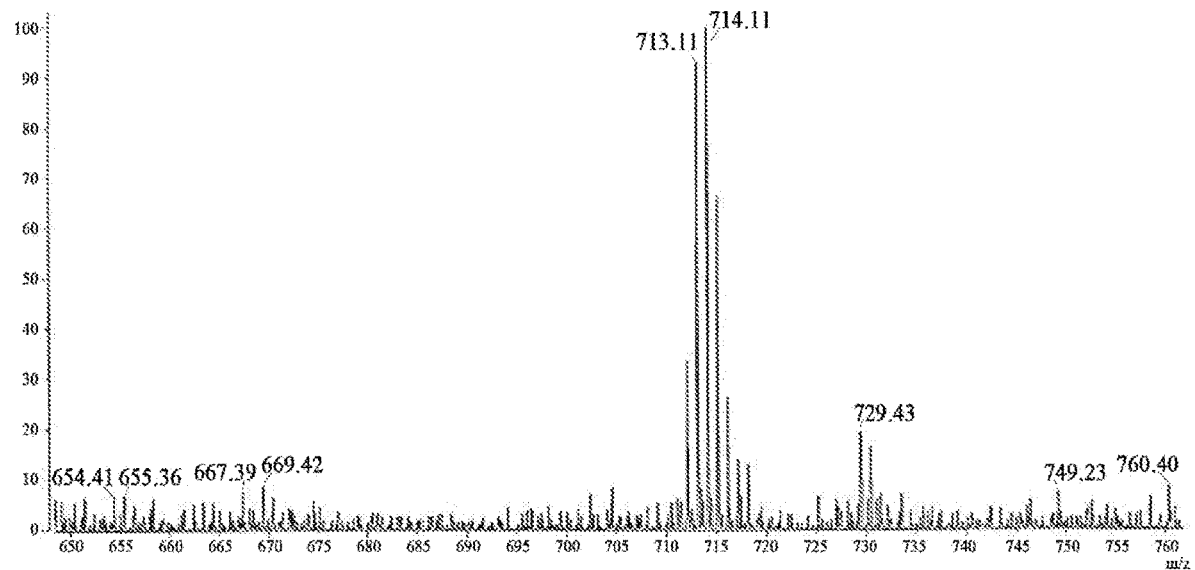
【FIG. 2f】
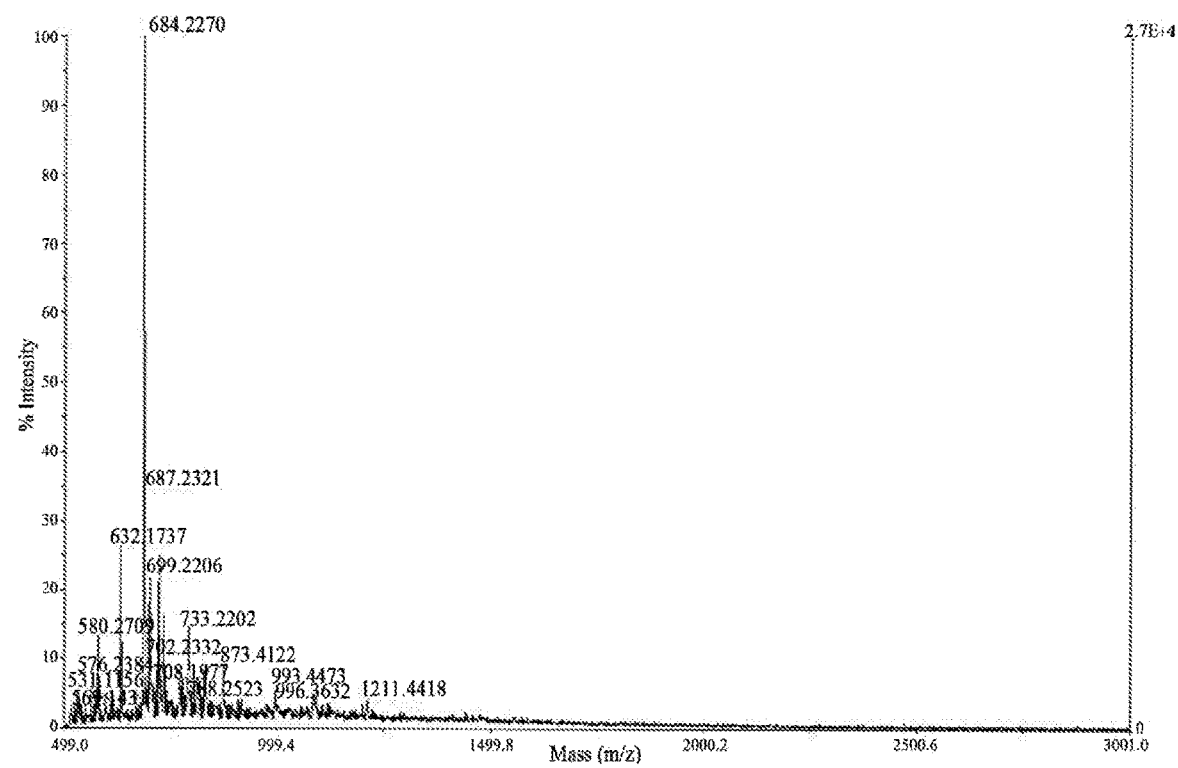

【FIG. 3a】
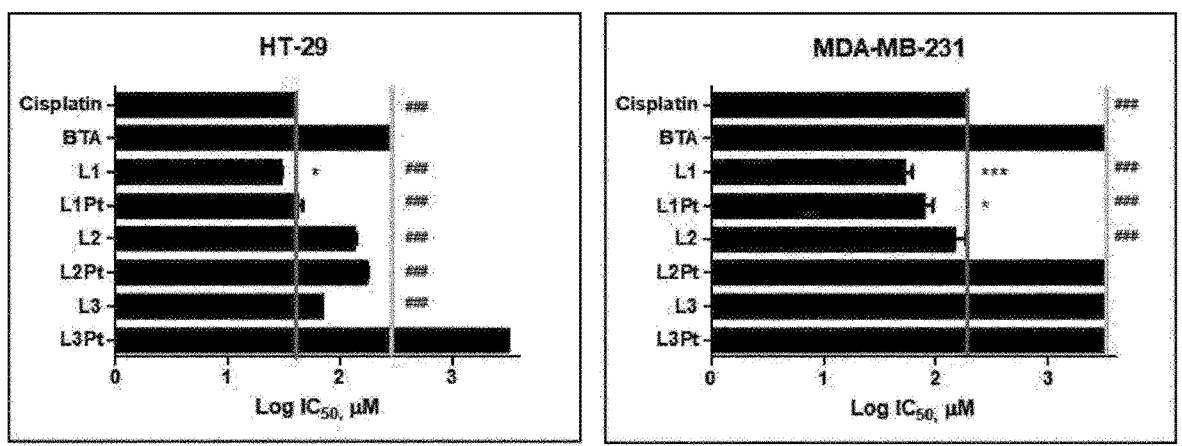
【FIG. 3b】
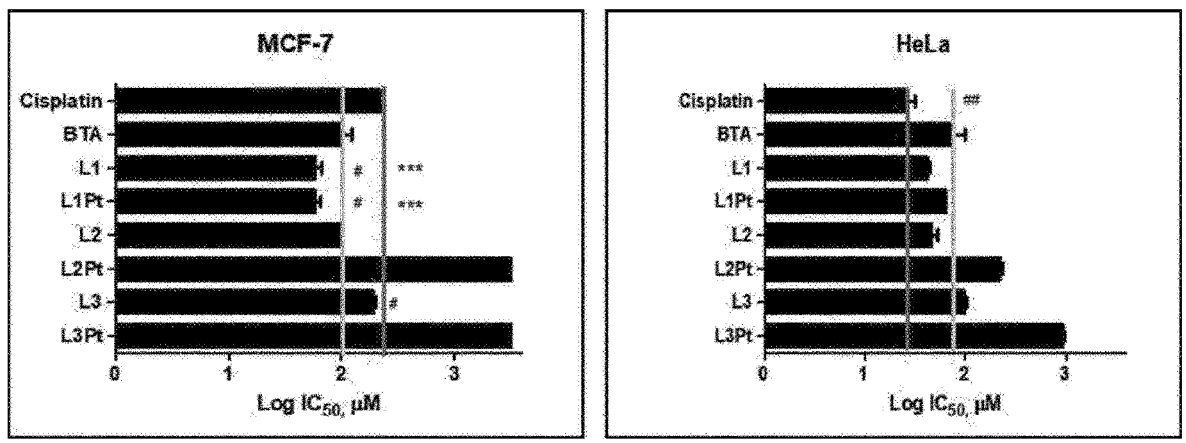

[FIG. 3c]
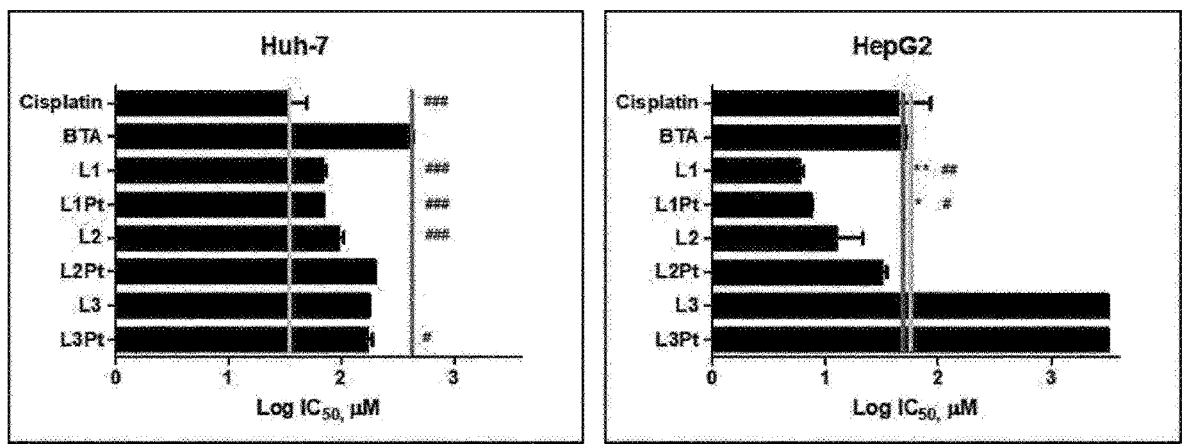
[FIG. 3d]
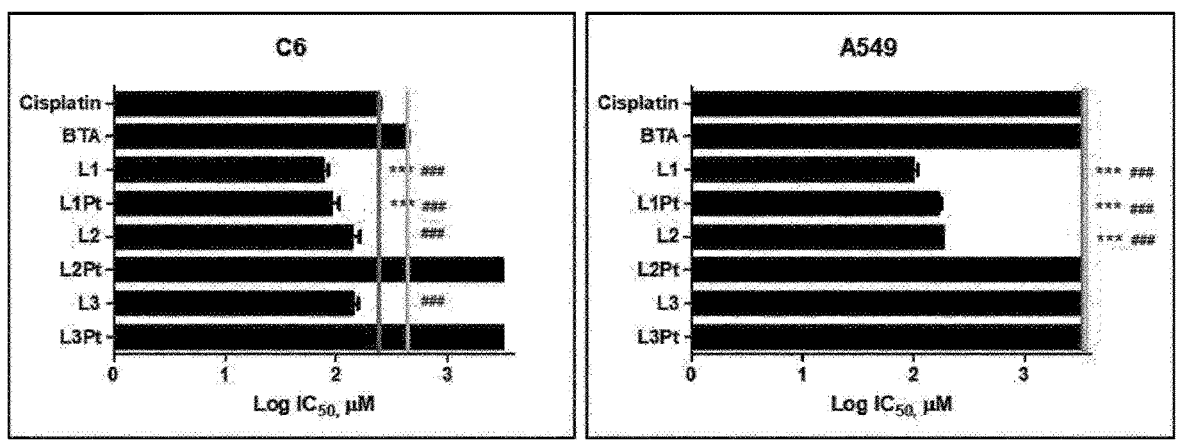

[FIG. 3e]
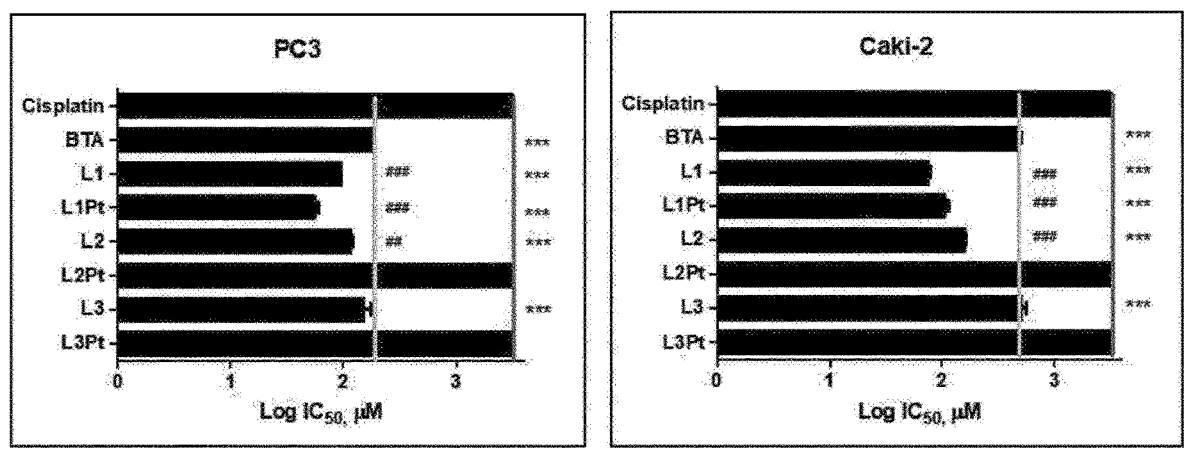

[FIG. 4]
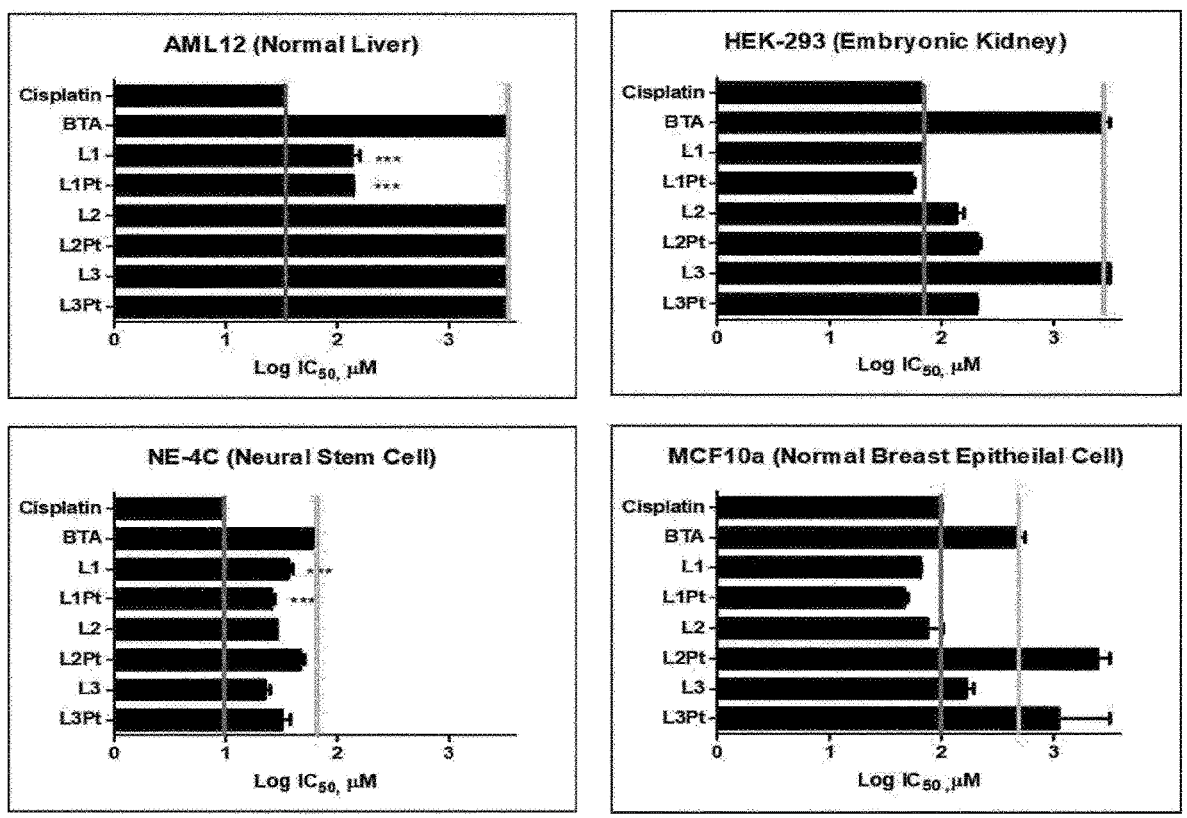

[FIG. 5a]
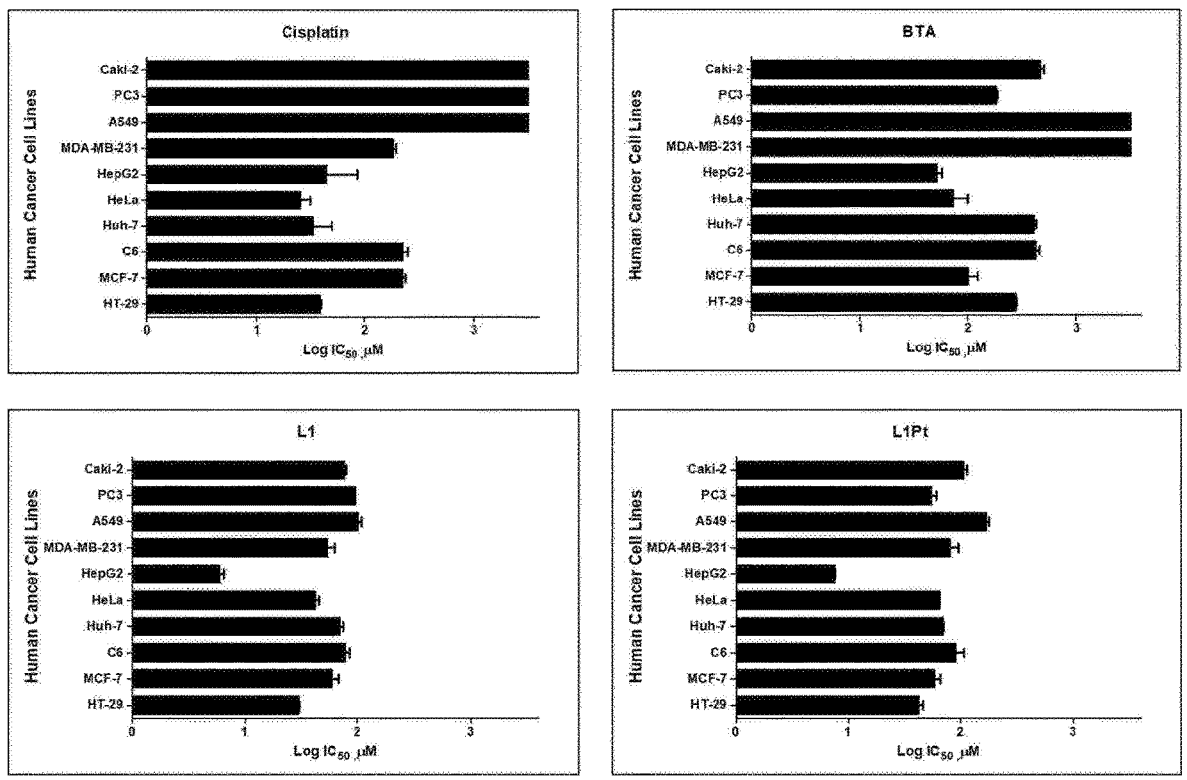

[FIG. 5b]
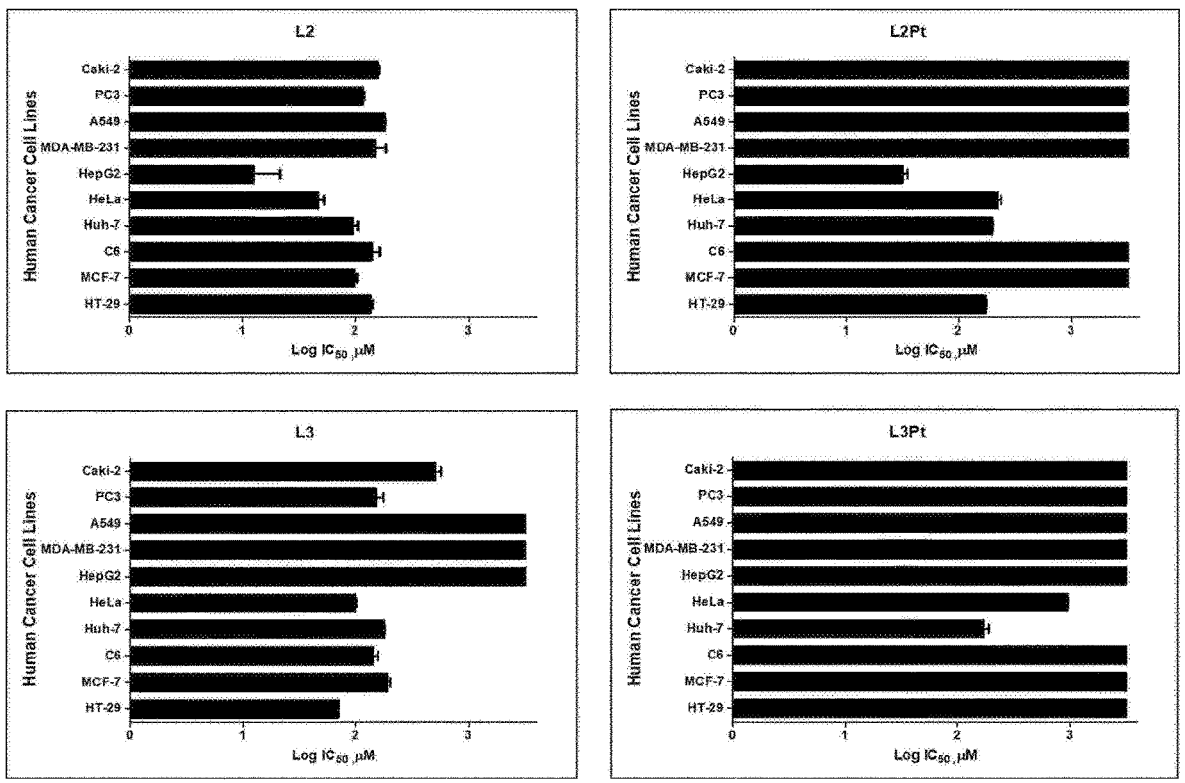

COMPOUND HAVING NOVEL STRUCTURE, COMPLEX COMPRISING SAME, ANTI-CANCER PHARMACEUTICAL COMPOSITION, AND ANTI-CANCER DRUG

CROSS REFERENCE TO RELATED APPLICATIONS

This application is a national phase under 35 U.S.C. § 371 of International Application No. PCT/KR2019/005531, filed May 9, 2019, which claims the benefit of priority to Korean Patent Application Serial Nos. 10-2018-0053674, filed May 10, 2018 and 10-2019-0053919, filed May 8, 2019.

FIELD OF THE INVENTION

The present disclosure relates to a compound having a novel structure, and more specifically, to a compound having a novel structure, a complex containing the same, a pharmaceutical composition having anticancer activity containing the compound or the complex, and an anticancer drug containing the compound or the complex or the composition.

DESCRIPTION OF RELATED ART

When an abnormality in a regulatory function of a cell occurs, abnormal cells that normally need to be killed do not die, but excessively proliferate, and invades surrounding tissues and organs to form a tumor (lump), thus destroying or transforming an existing structure. The tumor composed of undifferentiated cells that disregards an order and proliferates indefinitely within these tissues may be defined as cancer. A recent cancer incidence is increasing rapidly compared to the past, due to the rapid development of industry and changes in the global ecosystem and diet. For this reason, various anticancer drugs are being researched and developed.

Among them, cisplatin as a compound in which two chlorine and ammonia are coordinated with a platinum atom, is one of anticancer drugs widely used in cancer treatment. Cancer cells are characterized by continuous proliferation as they cannot inhibit cell division thereof. Since cisplatin inhibits cell division by blocking the reproductive ability of cancer cells by changes in the DNA sequence, it may prevent cancer cell proliferation and further prevent cancer from progressing. In other words, cisplatin exhibits anticancer activity. However, cisplatin is an excellent anticancer drug that is effective against many cancers, but unfortunately, it exhibits several side effects such as serious kidney damage. Further, it doesn't dissolve in water.

Various conventional anti-cancer substances including cisplatin effectively inhibit the growth of cancer cells, but sometimes they are toxic to normal cells. In particular, not only the pharmacological action varies depending on the anticancer substance and the type of cancer, but also various side effects due to toxicity are present, which is a problem in the treatment of cancer.

Accordingly, research and development of new anticancer substances that may exhibit effective anticancer effects against target specific cancers are continuously required.

SUMMARY OF THE INVENTION

One purpose of the present disclosure is to provide a compound with a novel structure with anticancer effect.

Another purpose of the present disclosure is to provide a pharmaceutical composition containing the compound.

Another purpose of the present disclosure is to provide a complex in which a compound having a novel structure with anticancer effect and a metal atom are coordinated with each other.

Another purpose of the present disclosure is to provide a pharmaceutical composition containing the complex.

Another purpose of the present disclosure is to provide an anticancer drug containing the pharmaceutical composition.

In one aspect, the present disclosure provides a compound having a structure represented by a following Chemical Formula 1:

[Chemical Formula 1]

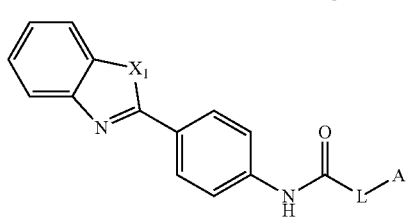

In the Chemical Formula 1, $X_1$ represents NH, O or S, L represents

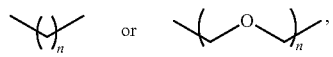

$(n = 0\ to\ 5)$

A represents one of following Chemical Formulas A-1 to A-3:

[Chemical Formula A-1]

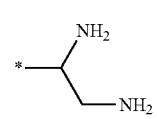

[Chemical Formula A-2]

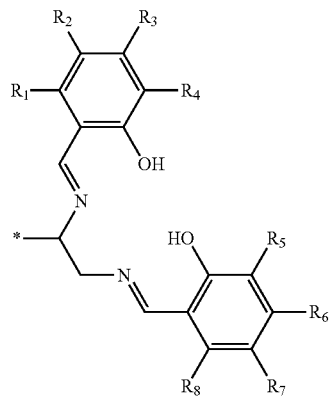

[Chemical Formula A-3]

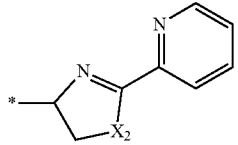

wherein in the Chemical Formula A-2, each of $R_1$ to $R_8$ independently represents H, $OCH_3$ or F, and in the Chemical Formula A-3, $X_2$ represents NH, O or S.

Preferably, the compound according to the present disclosure may have a structure represented by one of following Chemical Formulas 1-1 to 1-3:

[Chemical Formula 1-1]

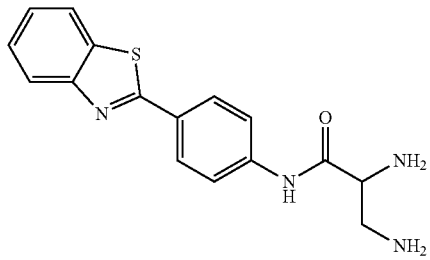

[Chemical Formula 1-2]

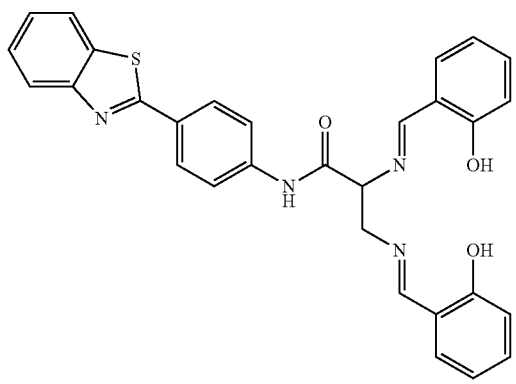

[Chemical Formula 1-3]

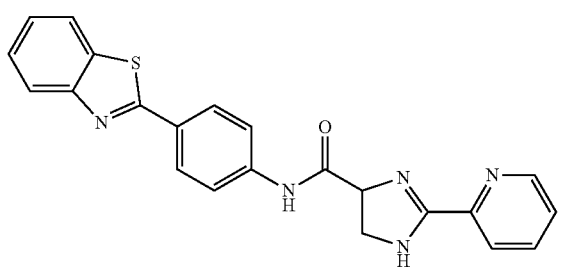

In another aspect, the present disclosure provides a pharmaceutical composition containing the compound of the Chemical Formula 1, wherein the pharmaceutical composition may contain a pharmaceutically acceptable carrier.

The composition is characterized by targeting cancer cells of at least one selected from a group consisting of colorectal cancer, breast cancer, liver cancer, brain glioma, lung cancer, prostate cancer, kidney cancer and cervical cancer, and having anticancer activity on the cancer cells.

When the compound has a structure of the Chemical Formula 1-1, the composition is characterized by having anticancer activity against colorectal cancer, breast cancer, liver cancer, brain glioma, lung cancer, prostate cancer and kidney cancer.

When the compound has a structure of Chemical Formula 1-2, the composition is characterized by having anticancer activity against colorectal cancer, breast cancer, liver cancer, brain glioma, lung cancer, prostate cancer and kidney cancer.

When the compound has a structure of Chemical Formula 1-3, the composition is characterized by having anticancer activity against colorectal cancer, breast cancer, brain glioma, prostate cancer and kidney cancer.

In still another aspect, the present disclosure provides a complex containing the compound according to the present disclosure having a structure represented by the Chemical Formula 1 as a ligand, and a metal atom coordinated to the ligand. The metal atom may be platinum (Pt).

In this connection, the complex may have a structure represented by one of following Chemical Formulas 2-1 to 2-3:

[Chemical Formula 2-1]

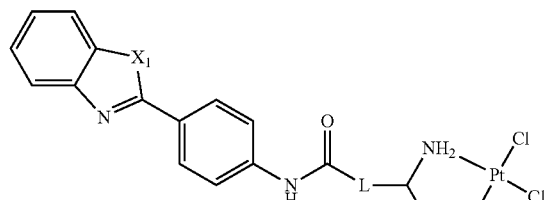

[Chemical Formula 2-2]

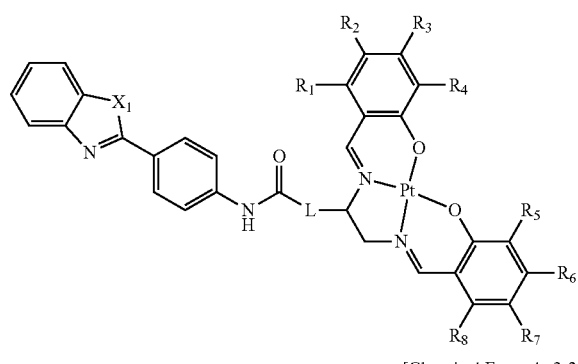

[Chemical Formula 2-3]

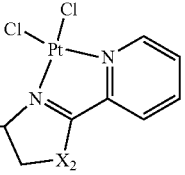

In the Chemical Formulas 2-1 to 2-3, L represents

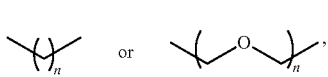

(n = 0 to 5)

each of $R_1$ to $R_8$ independently represents H, $OCH_3$ or F, each of $X_1$ and $X_2$ independently represents NH, O or S.

Preferably, the complex according to the present disclosure may be a complex characterized by having a structure represented by one of following Chemical Formulas 3-1 to 3-3:

[Chemical Formula 3-1]

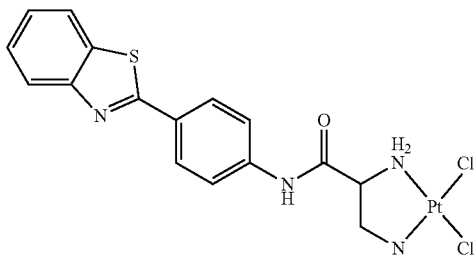

[Chemical Formula 3-2]

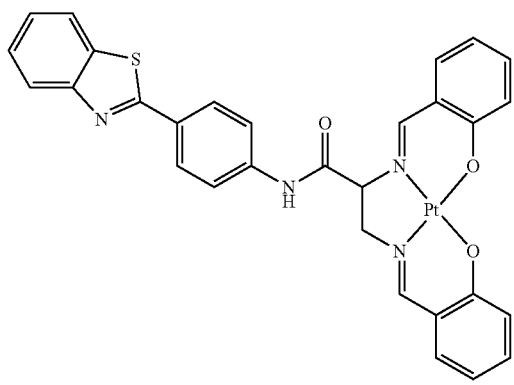

[Chemical Formula 3-3]

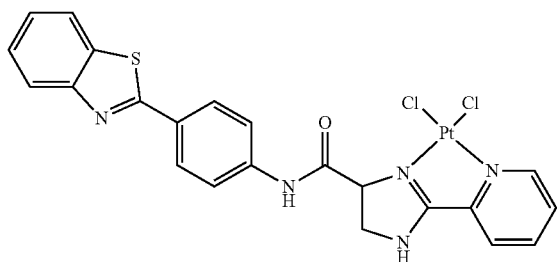

In still another aspect, the present disclosure provides a pharmaceutical composition containing the complex. The composition is characterized by targeting cancer cells of at least one selected from a group consisting of colorectal cancer, breast cancer, liver cancer, brain glioma, lung cancer, prostate cancer, kidney cancer and cervical cancer, and having anticancer activity on the cancer cells.

When the complex has a structure represented by the Chemical Formula 3-1, the composition is characterized by having anticancer activity against colorectal cancer, breast cancer, liver cancer, brain glioma, lung cancer, prostate cancer and kidney cancer.

When the complex has a structure represented by the Chemical Formula 3-2, the composition is characterized by having anticancer activity against colorectal cancer.

When the complex has a structure represented by the Chemical Formula 3-3, the composition is characterized by having anticancer activity against liver cancer.

In still another aspect, the present disclosure provides an anticancer drug containing, as an active ingredient, a compound according to the present disclosure as described above, the complex according to the present disclosure as described above or a pharmaceutical composition according to the present disclosure as described above.

According to the present disclosure, the compound having a novel structure, the complex containing the same, the pharmaceutical composition having anticancer activity containing the compound or the complex, and the anticancer drug containing the compound or the complex or the composition are provided. The compound has anticancer activity. Thus, the pharmaceutical composition containing the compound according to the present disclosure may target and kill cells of specific cancers such as colorectal cancer, breast cancer, liver cancer, brain glioma, lung cancer, prostate cancer, kidney cancer, and cervical cancer. That is, the composition has anticancer activity on the cancers. Further, according to the present disclosure, the complex according to the present disclosure in which the compound according to the present disclosure is coordinated with the metal atom is provided. Further, the pharmaceutical composition containing the complex is provided. The complex according to the present disclosure may exhibit a synergistic effect on the anticancer activity based on the novel structure of the compound according to the present disclosure and the metal atom coordinated thereto, thus exhibiting very excellent anticancer activity. Therefore, the pharmaceutical composition containing the complex according to the present disclosure has excellent anticancer activity. In this connection, the pharmaceutical composition containing the complex according to the present disclosure may target cells of specific cancers such as colorectal cancer, breast cancer, liver cancer, brain glioma, lung cancer, prostate cancer, kidney cancer, and cervical cancer, and have anticancer activity thereon. In addition, the anticancer drug containing the pharmaceutical composition according to the present disclosure has excellent anticancer activity.

BRIEF DESCRIPTION OF THE DRAWINGS

FIGS. 1a to 1f are diagrams for describing results of $^1$H NMR analysis of compounds L1, L2, and L3 according to Examples 1 to 3 of the present disclosure, and complexes L1Pt, L2Pt, and L3Pt according to Examples 4 to 6 of the present disclosure, respectively.

FIGS. 2a to 2f are diagrams for describing HR-FABMS analysis results of compounds L1, L2, and L3 according to Examples 1 to 3 of the present disclosure, and complex L1Pt, L2Pt, and L3Pt according to Examples 4 to 6 thereof, respectively.

FIGS. 3a to 3e and FIG. 4 show results of evaluation of properties of compounds L1 to L3 according to Examples 1 to 3 of the present disclosure and complexes L1Pt to L3Pt according to Examples 4 to 6 thereof together with those of cisplatin and benzothiazole aniline (BTA) as controls.

FIGS. 5a to 5b show results of comparing and analyzing effects of each of the compounds according to the present disclosure and cisplatin and BTA as controls in various cancer cell lines and normal cells.

DETAILED DESCRIPTIONS

Hereinafter, an embodiment of the present disclosure will be described in detail with reference to the accompanying drawings. The present disclosure may have various changes and various forms in terms of implementations thereof. Specific embodiments will be illustrated in the drawings and will be described in detail herein. However, it should be understood that the specific embodiments are not intended to limit the present disclosure thereto, and rather the present disclosure includes all of changes, equivalents, or substitutes included in the spirit and scope of the present disclosure. In describing the drawings, similar reference numerals have been used for similar elements.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A compound according to the present disclosure has a structure represented by the following Chemical Formula 1:

[Chemical Formula 1]

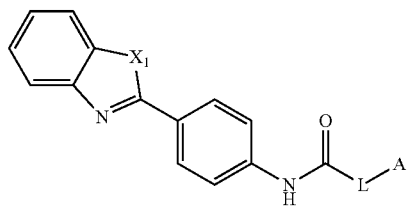

In the Chemical Formula 1, $X_1$ represents NH, O or S, L represents

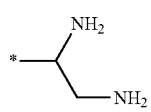

(n = 0 to 5)

A represents one of following Chemical Formulas A-1 to A-3:

[Chemical Formula A-1]

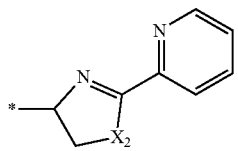

[Chemical Formula A-2]

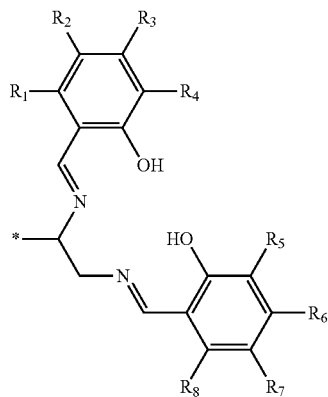

[Chemical Formula A-3]

wherein in the Chemical Formula A-2, each of $R_1$ to $R_8$ independently represents H, $OCH_3$ or F, and in the Chemical Formula A-3, $X_2$ represents NH, O or S, and * denotes a binding site.

For example, when in the Chemical Formula 1, $X_1$ is S, L is

(n = 1)

each of $R_1$ to $R_8$ in A is H and $X_2$ in A is NH, the Chemical Formula 1 may be represented by following Chemical Formulas 1-1 to 1-3. In the description of following examples, the Chemical Formula 1-1 is denoted as L1, Chemical Formula 1-2 is denoted as L2, and Chemical Formula 1-3 is denoted as L3.

[Chemical Formula 1-1]

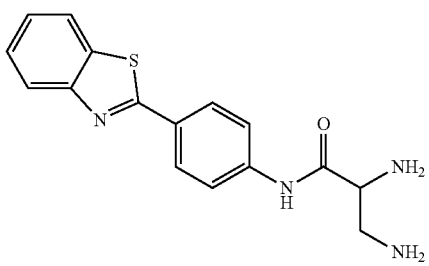

[Chemical Formula 1-2]

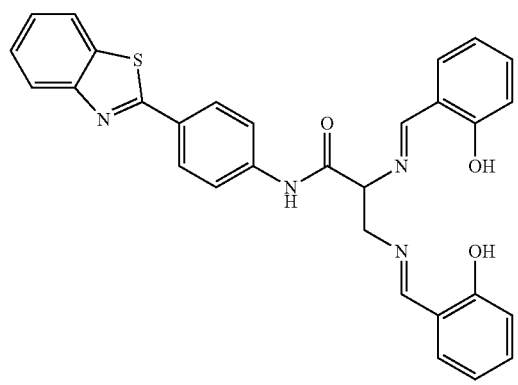

[Chemical Formula 1-3]

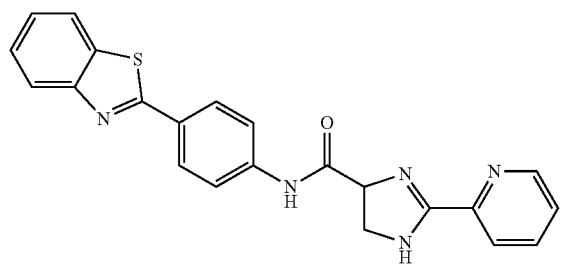

The compound according to the present disclosure may exhibit anticancer activity. Specifically, the compound according to the present disclosure may target cancer cells, inhibits the growth of cancer cells and kills the cancer cells and thus have an anticancer activity. In this connection, the compound according to the present disclosure may have anticancer activity against cancer cells of at least one among colorectal cancer, breast cancer, liver cancer, brain glioma, lung cancer, prostate cancer and kidney cancer. A more specific description thereof will be described later while describing the pharmaceutical composition according to the present disclosure.

Further, the compound according to the present disclosure may exhibit excellent solubility similar to that of cisplatin as an existing platinum-based anticancer drug.

In addition, the compound according to the present disclosure may chelate to a metal atom. In this connection, the metal atom may be platinum (Pt). For example, the chelation of the compound according to the present disclosure may be performed by reacting the compound according to the present disclosure with an aqueous solution of potassium tetrachloroplatinate (II) ($K_2PtCl_4$).

The complex according to the present disclosure contains one of the compounds according to the present disclosure as described above as a ligand and a metal atom that coordinates with the ligand.

In this connection, the metal atom may be a metal such as platinum. For example, when the metal atom is platinum, the complex according to the present disclosure may have a structure represented by one of following Chemical Formulas 2-1 to 2-3:

[Chemical Formula 2-1]

[Chemical Formula 2-2]

[Chemical Formula 2-3]

In the Chemical Formulas 2-1 to 2-3, L represents

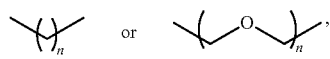

(n = 0 to 5)

each of $R_1$ to $R_8$ independently represents H, $OCH_3$ or F, each of $X_1$ and $X_2$ independently represents NH, O or S.

In an example, when the ligand is a compound represented by each of the Chemical Formulas 1-1 to 1-3, the complex may be represented by each of following Chemical Formulas 3-1 to 3-3. In the description of the following examples, Chemical Formula 3-1 is denoted as L1Pt, Chemical Formula 3-2 is denoted as L2Pt, and Chemical Formula 3-3 was denoted as L3Pt.

[Chemical Formula 3-1]

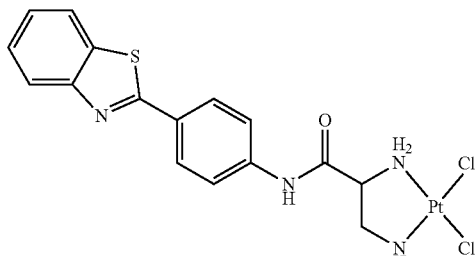

[Chemical Formula 3-2]

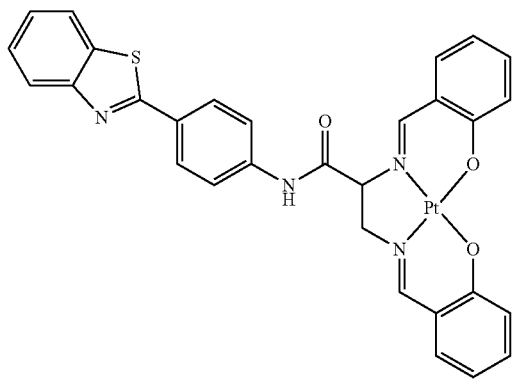

[Chemical Formula 3-3]

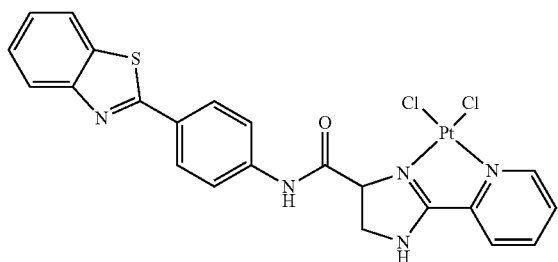

Since the complex according to the present disclosure contains the compound according to the present disclosure as described above as a ligand, it may exhibit excellent anticancer activity. Further, the complex according to the present disclosure is soluble in water, even though it contains a hydrophobic benzothiazole unit. Therefore, the complex according to the present disclosure may be used as a water-soluble anticancer substance.

In this connection, the complex according to the present disclosure may exhibit a specifically higher anticancer activity by targeting a specific cancer cell, as described referring to the compound according to the present disclosure. For example, the complex according to the present disclosure may have anticancer activity on cancer cells of at least any one among colorectal cancer, breast cancer, liver cancer, brain glioma, lung cancer, prostate cancer, and kidney cancer. For example, the complex represented by the Chemical Formula 3-1 may have excellent anticancer activity on all of colorectal cancer, breast cancer, liver cancer, brain glioma, lung cancer, prostate cancer and kidney cancer. The complex represented by the Chemical Formula 3-1 may have excellent anticancer activity on cancer cells of prostate cancer in that the complex targets cancer cells of prostate cancer more reliably than the ligand compound itself does. Further, the complex represented by the Chemical Formula 3-2 may have excellent anticancer activity on colorectal cancer. In addition, the complex represented by the Chemical Formula 3-1 may have excellent anticancer activity on liver cancer. The specific cancer was specifically mentioned and described above. However, this is intended to indicate that the complex according to the present disclosure has a higher anticancer activity on the specific cancer as mentioned above. This is not intended to indicate that the complex according to the present disclosure does not have anticancer activity on cancer other than the cancers as mentioned above.

As described above, the compound according to the present disclosure and the complex containing the compound have excellent anticancer activity and may be used as anticancer substances. In particular, the compounds and complexes according to the present disclosure may exhibit excellent anticancer activity by specifically targeting the specific cancer cells due to their structure, and thus may be used as anticancer substances targeting the specific cancer cells. Accordingly, due to such characteristics, the pharmaceutical composition containing the compound according to the present disclosure and/or the complex according to the present disclosure containing the compound of the present disclosure as a ligand may be provided.

For example, the pharmaceutical composition according to the present disclosure contains an effective amount of the compound according to the present disclosure and a pharmaceutically acceptable carrier, and targets the cancer cells and has anticancer activity on the cancer cells. In this connection, the cancer against the composition has anticancer activity may include at least one of colorectal cancer, breast cancer, liver cancer, brain glioma, lung cancer, prostate cancer, and kidney cancer.

For example, when the pharmaceutical composition according to the present disclosure contains a compound of the Chemical Formula 1-1, that is, a compound in which A in Chemical Formula 1 has a structure

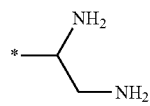

represented by the Chemical Formula A-1, the composition targets at least any one of colorectal cancer, breast cancer, liver cancer, brain glioma, lung cancer, prostate cancer, and kidney cancer, and may have excellent anticancer activity thereon. Compared to cisplatin and BTA, the pharmaceutical composition containing the compound of the Chemical Formula 1-1 according to the present disclosure has an excellent anticancer activity against colorectal cancer, breast cancer, liver cancer, brain glioma, lung cancer, prostate cancer and kidney cancer. In particular, it may have excellent anticancer activity against colorectal cancer, breast cancer, liver cancer, brain glioma, lung cancer, prostate cancer and kidney cancer.

Further, when the pharmaceutical composition according to the present disclosure contains a compound of the Chemical Formula 1-2, that is, a compound in which A in Chemical Formula 1 has a structure

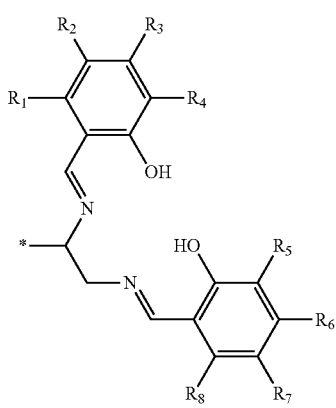

represented by the Chemical Formula A-2, the composition targets at least any one of colorectal cancer, breast cancer, liver cancer, brain glioma, lung cancer, prostate cancer, and kidney cancer, and may have excellent anticancer activity thereon. The pharmaceutical composition containing the compound of the Chemical Formula 1-2 according to the present disclosure has superior anticancer activity on colorectal cancer, breast cancer, liver cancer, brain glioma, lung cancer, prostate cancer and kidney cancer, compared to cisplatin and BTA. In particular, it may have excellent anticancer activity against liver cancer, brain glioma, lung cancer, prostate cancer and kidney cancer.

In addition, when the pharmaceutical composition according to the present disclosure contains a compound of the Chemical Formula 1-3, that is, a compound in which A in Chemical Formula 1 has a structure

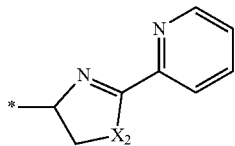

represented by the Chemical Formula A-3, the composition targets at least any one of colorectal cancer, breast cancer, brain glioma, prostate cancer, and kidney cancer, and may have excellent anticancer activity. The pharmaceutical composition containing the compound of the Chemical Formula 1-3 according to the present disclosure may have very excellent anticancer activity against brain glioma, compared to cisplatin and BTA.

In another example, the pharmaceutical composition according to the present disclosure contains an effective amount of the complex containing the compound according to the present disclosure as a ligand and a pharmaceutically acceptable carrier.

When the pharmaceutical composition containing the complex according to the present disclosure contains a compound of the Chemical Formula 3-1, that is, a compound in which A of the ligand of the complex has a structure

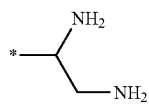

represented by the Chemical Formula A-1, the composition targets at least any one of colorectal cancer, breast cancer, liver cancer, brain glioma, lung cancer, prostate cancer, and kidney cancer, and may have excellent anticancer activity thereon. Compared to cisplatin and BTA, the pharmaceutical composition containing the compound of the Chemical Formula 3-1 according to the present disclosure has an excellent anticancer activity against colorectal cancer, breast cancer, liver cancer, brain glioma, lung cancer, prostate cancer and kidney cancer. In particular, it may have excellent anticancer activity against colorectal cancer, breast cancer, liver cancer, brain glioma, lung cancer, prostate cancer and kidney cancer.

Further, when the pharmaceutical composition containing the complex according to the present disclosure contains a compound of the Chemical Formula 3-2, that is, a compound in which A of the ligand of the complex has a structure

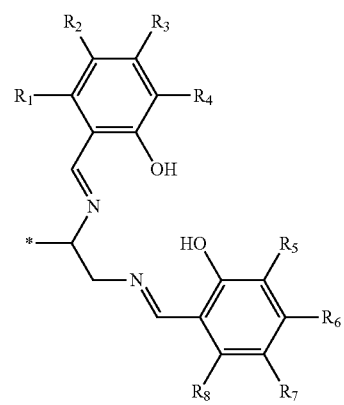

represented by the Chemical Formula A-2, the composition targets colorectal cancer, and may have excellent anticancer activity thereon.

In addition, when the pharmaceutical composition containing the complex according to the present disclosure contains a compound of the Chemical Formula 3-3, that is, a compound in which A of the ligand of the complex has a structure

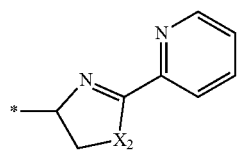

represented by the Chemical Formula A-3, the composition targets liver cancer and may have excellent anticancer activity.

The examples where the pharmaceutical composition according to the present disclosure contains the compound according to the present disclosure or the complex according to the present disclosure have been described above. However, the pharmaceutical composition according to the present disclosure may contain both of the compound according to the present disclosure and the complex according to the present disclosure.

Further, the anticancer drug according to the present disclosure contains at least one of the compounds according to the present disclosure as described above and the complexes according to the present disclosure as described above or the pharmaceutical composition containing the compound and/or the complex as described above. Thus, the drug targets cancer cells and has anticancer activity on the cancer cells. In this connection, in an example, the anticancer drug according to the present disclosure may be an anticancer drug having anticancer activity by targeting at least any one of colorectal cancer, breast cancer, liver cancer, brain glioma, lung cancer, prostate cancer, and kidney cancer.

Hereinafter, specific examples related to the compound and complex according to the present disclosure, a method of preparing the same, and anticancer effects thereof will be described in more detail.

Synthesis of Compounds and Complexes According to the Present Disclosure: L1, L2, L3, L1Pt, L2Pt, and L3Pt

(1) Synthesis of Compound 1

While adding sodium hydrogen carbonate (NaHCO$_3$) (9.07 g, 108 mmol) to 2,3-diaminopropionic acid monohydrobromide (5 g, 27 mmol) dissolved in 108 mL of tertiary distilled water, the mixture solution was stirred. After completely dissolving, an ice-bath was installed to cool the mixed solution to 0° C. Then, di-tert-butyl dicarbonate (14.73 g, 67.5 mmol) dissolved in dioxane (67.5 mmol) was slowly added dropwise to the cooled solution. Then, the mixture was stirred at 0° C. for 30 minutes, and then stirred at room temperature overnight. Then, we installed an ice-bath again such that the mixture was cooled to 0° C. Then, the mixture was acidified to a pH of 2 to 3 by adding a 3 M aqueous hydrochloric acid solution thereto. Then, a product was extracted as an organic layer using water, brine, and ethyl acetate. Then, anhydrous magnesium sulfate (MgSO$_4$) was added to the organic layer to remove the remaining water, and was then filtered. The solvent was removed from the filtered liquid under reduced pressure to obtain a colorless oil. Then, the oil was dried under reduced pressure to obtain a white solid, that is, 2,3-bis-tert-butoxycarbonylamino-propionic acid (hereinafter, compound 1) (yield 7.4 g, 95%).

To identify the synthesis of the compound 1, a thin membrane chromatography plate was used in a developer of butanol/water/acetic acid (8:1:1). An alcohol solution containing 2% ninhydrin was used for detection.

Results of IR and $^1$H NMR analysis of the synthesized compound 1 are as follows: IR (KBr, cm$^{-1}$): 3500-3300 (st. OH, st. NH), 2977-2931 (st. CH), 1741 (st. C=O acid), 1695 (st. C=O), 1527 (ds NH, st. si. NC=O), 1443 (dip NH). $^1$H-NMR (400 MHz, CDCl$_3$) δ (ppm): 1.45 (s, 18H, CH$_3$), 3.55 (m, 2H, CH$_2$), 4.12 (s, 1H, CH), 4.27-5.17 (m, 1H, NH), 5.85 (s, 1H, OH), 2.05 (s, 1H, NH). Anal. Calcd for C$_{13}$H$_{24}$O$_6$N$_2$·½EtOAc: C, 51.71; H, 8.04; N, 8.10. Found: C, 51.87; H, 8.15; N, 7.75.

Further, the synthesis reaction of the compound 1 may be summarized and represented as Reaction Formula 1 below:

[Reaction Formula 1]

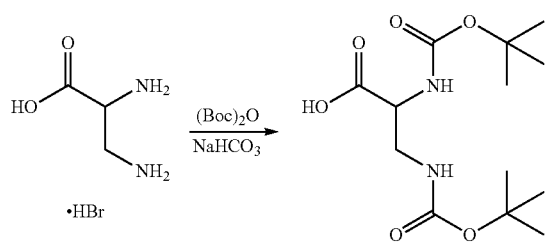

(2) Synthesis of Compound 2

Benzothiazole aniline (5.20 g, 23.01 mmol) dissolved in pyridine (20 ml) was slowly added to the compound 1 (7.00 g, 23.01 mmol, 1.0 eq) dissolved in pyridine (40 ml). Then, after the mixture was further stirred for 10 minutes, triphenyl phosphite (7.13 ml, 23.01 mmol) was added thereto. Then, the reaction solution was stirred at 80° C. for 3 hours, and then stirred at room temperature overnight. Then, the resulting powder was filtered while being washed with distilled water and acetone. Then, the filtered precipitate was recrystallized using anhydrous acetonitrile. Thus, a white solid, that is, [2-(4-benzothiazol-2-ylphenylcarbamoyl)-2-tert-butoxycarbonylamino-ethyl]-carbamic acid tert butyl ester) (hereinafter, compound 2) was obtained (yield: 9.6 g, 81.4%).

The results of $^1$H NMR analysis of the synthesized compound 2 are as follows: $^1$H NMR (400 MHz, CDCl$_3$): δ=9.28 (s, 1H, NH) 8.06-8.01 (m, 3H, BTA), 7.89-7.85 (d, 1H, BTA), 7.68-7.64 (d, 2H, BTA), 7.49-7.44 (t, 1H, BTA), 7.38-7.33 (t, 1H, BTA), 5.97-5.93 (s, 2H, NH), 4.02-3.98 (d, 1H, CH) 3.57-3.41 (m, 2H, CH$_2$), 1.50-1.40 (d, 18H, CH$_3$) Anal. Calcd for C$_{26}$H$_{32}$N$_4$O$_5$S: C, 60.92; H, 6.29; N, 10.93; S, 6.26. Found: C, 60.05; H, 6.36; N, 10.60; S, 5.98.

Further, the synthesis reaction of the Compound 2 may be summarized and represented as Reaction Formula 2 below:

[Reaction Formula 2]

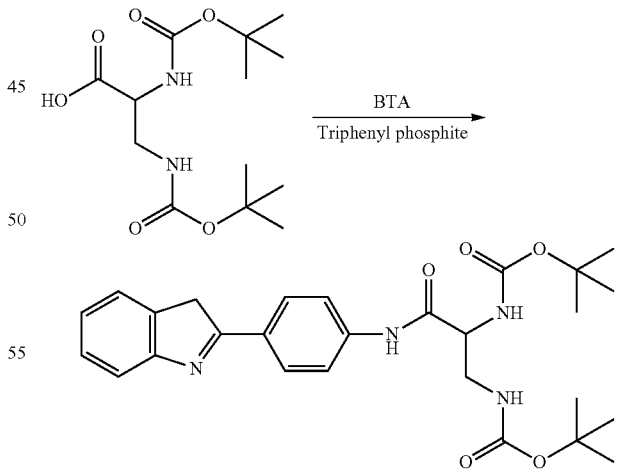

(3) Synthesis of Compound According to Example 1 of the Present Disclosure: L1 (Chemical Formula 1-1)

After installing an ice-bath, a trifluoroacetic acid solution (10 ml) was slowly added to the compound 2 (1.5 g, 2.92 mmol) dissolved in dichloromethane (DCM) at 0° C. Then, the solvent was removed from the resulting yellow solution, and then, ether was added thereto to obtain a precipitate. Then, the resulting precipitate was further washed three times with ether and then filtered. Thus, a light yellow solid, that is, a compound according to Example 1 of the present disclosure, that is, 2,3-diamoniumtrifluoroacetate-N-(4-benzothiazol-2-yl-phenyl)-propionamide) (hereinafter, L1) was obtained (yield: 0.82 g, 90%).

The synthesis reaction of the compound L1 according to Example 1 of the present disclosure may be summarized as Reaction Formula 3 below:

[Reaction Formula 3]

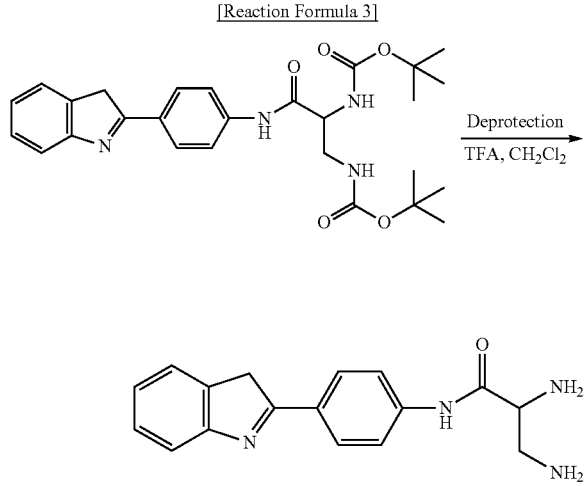

(4) Synthesis of Compound According to Example 2 of the Present Disclosure: L2 (Chemical Formula 2-1)

The compound according to Example 1 of the present disclosure, that is, L1 (540 mg, 1 mmol) was dissolved in anhydrous ethanol, and salicylaldehyde (0.270 ml, 2.1 mmol) was slowly dropped thereto while stirring at 40° C. Then, the mixture was stirred at 60° C. for 3 hours, and then cooled to room temperature. Then, the resulting suspension was washed with ethanol and diethylether, and then filtered. Thus, a white solid, that is, the compound according to Example 2 of the present disclosure, that is, N-(4-benzothiazol-2-yl-phenyl)-2,3-bis-[(2-hydroxy-benzylidene)-amino]-propionamide) (hereinafter, L2) was obtained (yield: 0.43 g, 82%).

The synthesis reaction of the compound L2 according to Example 2 of the present disclosure may be summarized as Reaction Formula 4 below:

[Reaction Formula 4]

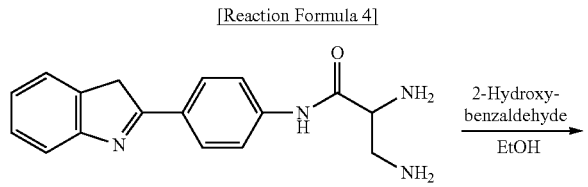

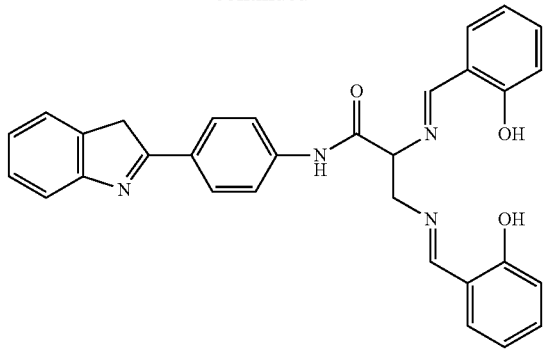

(5) Synthesis of Compound According to Example 3 of the Present Disclosure: L3 (Chemical Formula 1-3)

2-pyridinecarboxaldehyde (0.3 ml, 2.80 mmol) was added dropwise at 0° C. to a solution in which the compound L1 according to Example 1 of the present disclosure (1.58 g, 2.94 mmol) was dissolved in dry tetrahydrofuran (dry THF) (20 ml). Then, N-bromosuccinimide (0.52 g, 2.94 mmol) was added to the mixture, followed by reaction at room temperature for 18 hours. After the reaction was completed, the reaction mixture was extracted using saturated sodium hydrogen carbonate ($NaHCO_3$) solution and DCM. Then, the solvent in an organic extracted layer was dehydrated with anhydrous sodium sulfate, and then distilled under reduced pressure to obtain an oily product. Then, to solidify the oil product, the oil product was precipitated with diethyl ether. Thus, a pale yellow solid as the compound according to Example 3 of the present disclosure, that is, N-(4-(benzo[d]thiazol-2-yl)phenyl)-2-(pyridin-2-yl)-4,5-dihydro-1H-imidazole-4-carboxamide (hereinafter, L3) was obtained (yield: 0.72 g, 60%).

The synthesis reaction of the compound L3 according to Example 3 of the present disclosure may be summarized as Reaction Formula 5 below:

[Reaction Formula 5]

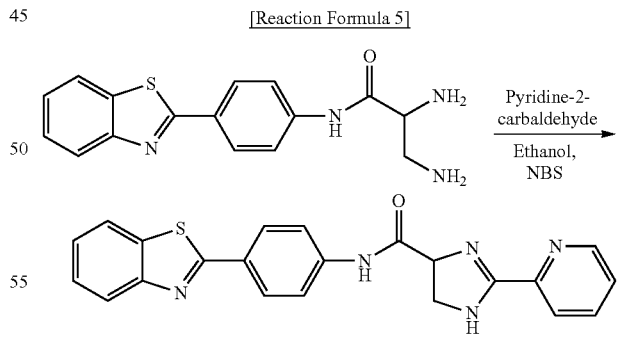

(6) Synthesis of Complex According to Example 4 of the Present Disclosure: L1Pt (Chemical Formula 3-1)

Potassium tetrachloroplatinate (II) ($K_2PtCl_4$) aqueous solution (145 mg, 0.35 mmol, 15 ml) was added dropwise to a solution in which the L1 compound according to Example 1 of the present disclosure L1 (110 mg, 0.35 mmol) was dissolved in methanol (MeOH) (10 ml). The reaction mixture was subjected to dark reaction at room temperature and under nitrogen gas condition for 18 hours. Then, the orange precipitate was filtered, and washed with distilled water, MeOH, and diethyl ether. Subsequently, the precipitate was distilled under reduced pressure and dried to obtain a pale yellow solid product as a complex (hereinafter, L1Pt) according to Example 4 of the present disclosure (yield: 0.108 g, 53%).

The synthesis reaction of the complex L1Pt according to Example 4 of the present disclosure may be summarized and represented by a following Reaction Formula 6:

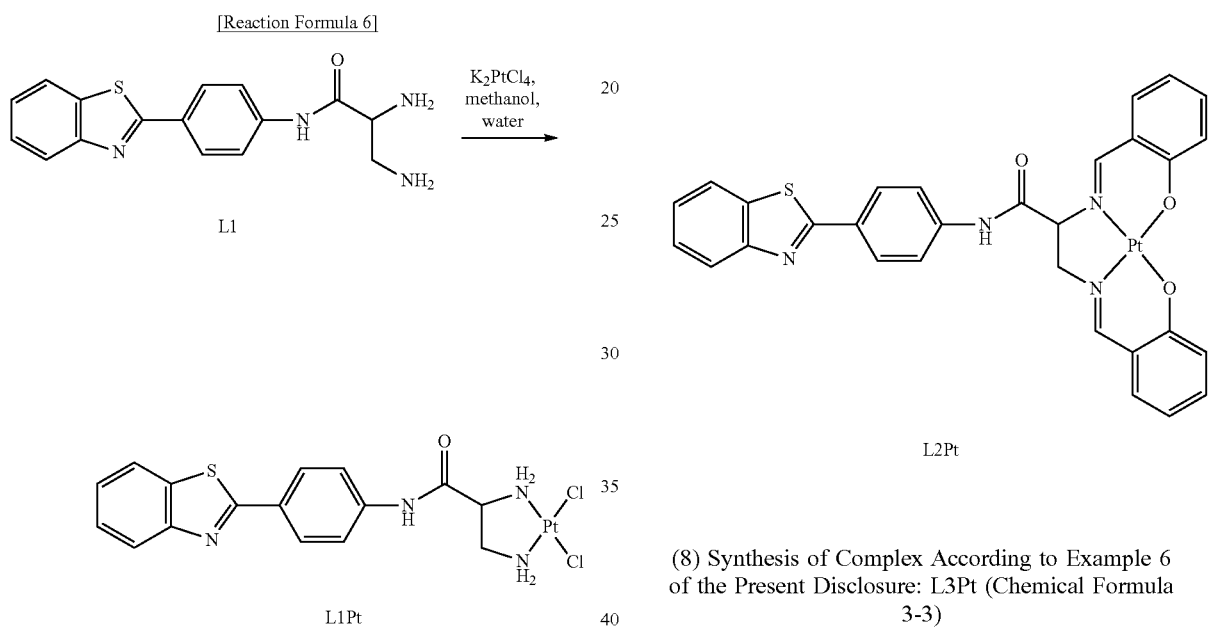

(7) Synthesis of Complex According to Example 5 of the Present Disclosure: L2Pt (Chemical Formula 3-2)

Potassium carbonate (185 mg, 1.35 mmol) was slowly added to a solution in which the compound L2 according to Example 2 of the present disclosure (350 mg, 0.67 mmol) was dissolved in DMF (10 ml). Then, an aqueous K2PtCl4 solution (280 mg, 0.67 mmol, 15 ml) was added dropwise to the mixture solution, followed by reaction at 60° C. for 18 hours. After the reaction was completed, the reaction mixture was cooled to room temperature and was filtered, and then washed with distilled water, MeOH, and diethyl ether. Subsequently, the reaction product was distilled under reduced pressure to obtain a pale yellow solid product as a complex (hereinafter, L2Pt) according to Example 5 of the present disclosure (yield: 0.234 g, 48%).

The synthesis reaction of the complex L2Pt according to Example 5 of the present disclosure may be summarized as Reaction Formula 7 below:

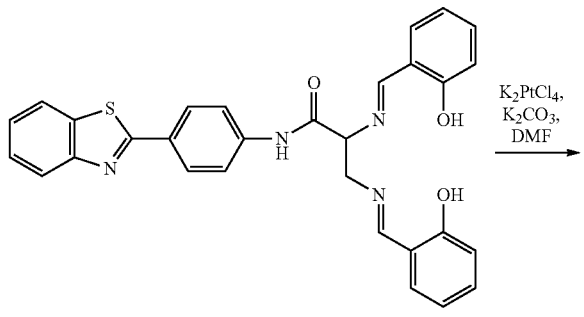

(8) Synthesis of Complex According to Example 6 of the Present Disclosure: L3Pt (Chemical Formula 3-3)

After dissolving the compound L3 (400 mg, 1.00 mmol) according to Example 3 of the present disclosure in anhydrous MeOH (25 ml), an aqueous K₂PtCl₄ solution (456 mg, 1.10 mmol, 20 ml) was added dropwise to the mixture solution. Then, the mixture solution was subjected to a dark reaction at 50° C. under nitrogen gas condition. After the reaction is complete, the reaction product was filtered, and washed with secondary distilled water, MeOH, and diethyl ether, and then was dried to obtain a pale yellow solid product as a complex (hereinafter, L3Pt) according to Example 6 of the present disclosure (yield: 0.278 g, 42%).

The synthesis reaction of the complex L3Pt according to Example 6 of the present disclosure may be summarized as Reaction Formula 8 below:

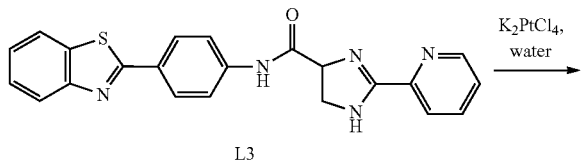

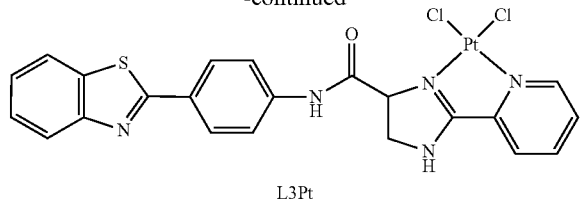

L3Pt

The synthesis reaction of the compound 1 and the compound 2 according to the present disclosure, and the compounds and the complexes according to Examples 1 to 6 of the present disclosure: L1, L2, L3, L1Pt, L2Pt, and L3Pt may be summarized and represented as Reaction Formula 9 below:

present disclosure, L1, L2, L3, L1Pt, L2Pt, and L3Pt were carried out. The results are shown in graphs in FIGS. 1a to 1f and 2a to 2f, respectively.

FIGS. 1a to 1f are diagrams for describing the results of $^1$H NMR analysis of the compounds L1, L2, and L3 according to Examples 1 to 3 of the present disclosure, and the complexes L1Pt, L2Pt, and L3Pt according to Examples 4 to 6, respectively. FIGS. 2a to 2f are diagrams for describing the HR-FABMS analysis results of compounds L1, L2, and L3 according to Examples 1 to 3 of the present disclosure, and the complexes L1Pt, L2Pt, and L3Pt according to Examples 4 to 6, respectively.

Specific results of $^1$H NMR analysis of the compounds L1, L2, and L3 according to Examples 1 to 3 of the present disclosure, and the complexes L1Pt, L2Pt, and L3Pt according to Examples 4 to 6 thereof are as follows:

[Reaction Formula 9]

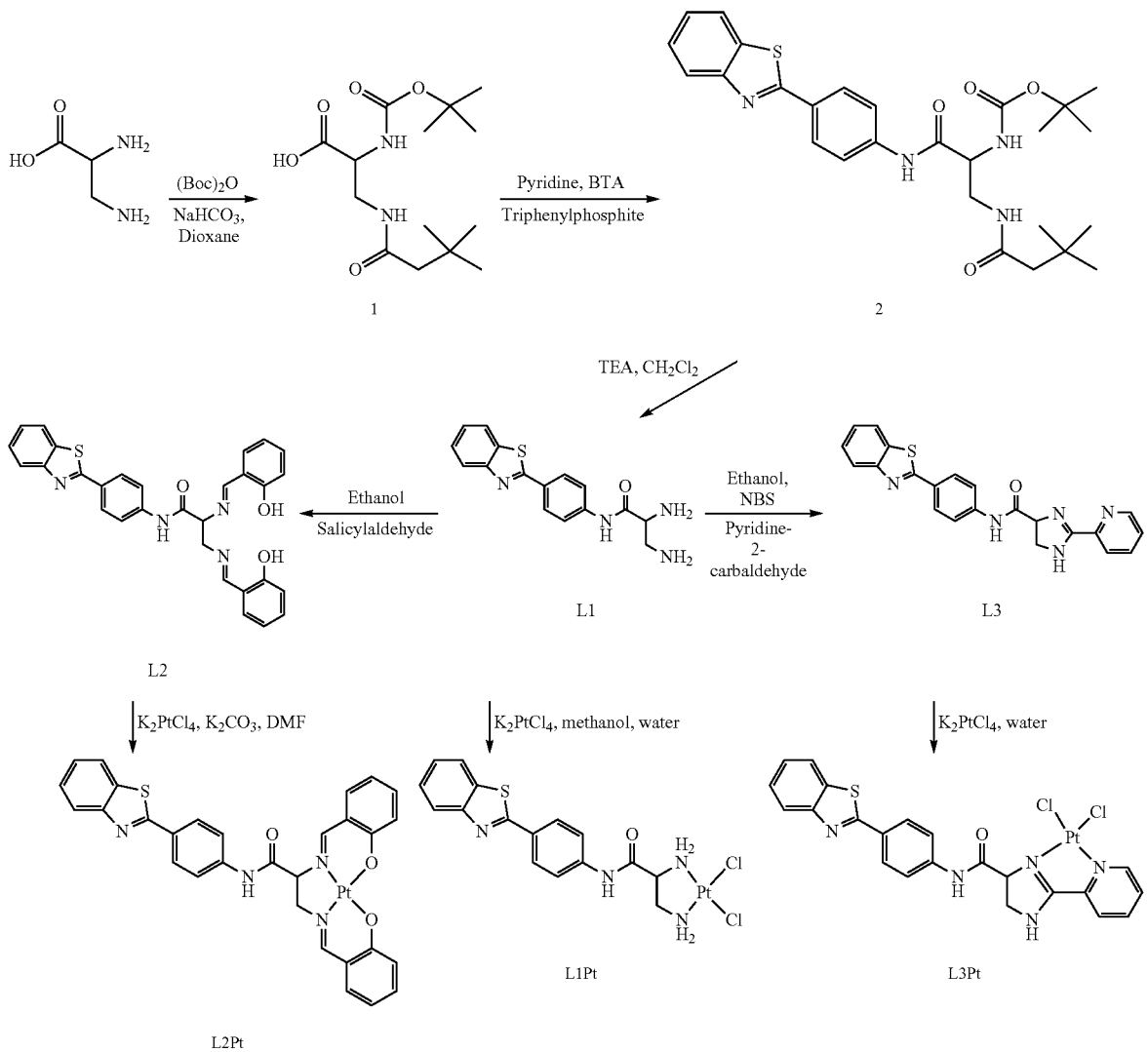

Analysis of compounds and complexes according to the present disclosure: L1, L2, L3, L1Pt, L2Pt, L3Pt $^1$H NMR and HR-FABMS (High resolution fast-atom bombardment mass spectrometry) analysis of the compounds and complexes according to Examples 1 to 6 of the $^1$H NMR (MeOH-d$_4$) of L1: δ=8.75 (s, 1H, NH), 8.01-7.99 (d, 2H, BTA), 7.9-7.89 (d, 2H, BTA), 7.82-7.78 (d, 2H, BTA), 7.45 (t, 1H, BTA), 7.35 (t, 1H, BTA), 4.43 (t, 1H, CH), 3.62-3.55 (dd, 1H, CH$_2$), 3.51-3.44 (dd, 2H, CH$_2$), 1.94 (s, 2H, NH). Anal. Calcd for $C_{16}H_{16}N_4OS \cdot 3CF_3COOH$: C, 40.37; H, 2.93; N, 8.56; S, 4.90. Found: C, 40.74; H, 2.68; N, 8.86; S, 5.26. FABMS: m/z (%) 313.1121 [M+H]$^+$.

$^1$H NMR (400 MHz, CDCl$_3$) of L2: δ=12.8 (s, 2H, Ar—OH) 12.01 (s, 1H, NH) 8.45 (s, 1H, CH) 8.36 (s, 1H, CH) 8.07-8.01 (m, 3H, BTA), 7.90-7.86 (d, 1H, BTA), 7.71-7.66 (d, 2H, BTA), 7.49-7.44 (t, 1H, BTA), 7.41-7.38 (t, 1H, BTA) 7.36-7.25 (m, 3H, Ar—CH) 7.22-7.18 (d, 1H, Ar—CH) 7.04-6.81 (m, 4H, Ar—CH) 4.42-4.36 (m, 2H, CH$_2$) 4.09-3.03 (m, 1H, CH). FT-IR: (KBr, cm$^{-1}$)=3299.9 w, 1665 s, 1633 s, 1524 s, 1407 s, 749 s. LC/MS: m/z (%): 521.2 (100.0%). Anal. Calcd for $C_{30}H_{24}N_4O_3S \cdot \frac{1}{2}H_2O$: C, 68.06; H, 4.76; N, 10.58; S, 6.06. Found: C, 68.08; H, 4.59; N, 10.62; S, 6.24. FABMS: m/z (%) 521.1645 [M+H]$^+$.

$^1$H NMR (500 MHz, CDCl$_3$) of L3: δ=9.56 (br, 1H, NH), 9.21 (s, 1H, NH), 8.64 (d, 1H, CH-Py), 8.37 (d, 1H, CH-Py), 8.12-8.04 (m, 3H, BTA), 7.88-7.82 (m, 3H, BTA), 7.48 (t, 1H, BTA), 7.37 (t, 1H, BTA), 7.16 (t, 1H, CH-Py), 6.99 (t, 1H, CH-Py), 5.07 (t, 1H, CH), 4.16-3.74 (d, 2H, CH$_2$). Anal. Calcd for $(C_{22}H_{17}N_5OS \cdot 1.5H_2O)$: C, 61.86; H, 4.74; N, 16.40; S, 7.50. Found: C, 62.32; H, 3.97; N, 15.64; S, 7.54. FABMS: m/z (%): 400.1232 [M+H]$^+$ (100).

$^1$H NMR (500 MHz, DMSO-d$_6$) of L1Pt: δ=11.03 (w, 1H, NH), 8.77-8.51 (w, 2H, NH$_2$), 8.17-7.99 (m, 4H, BTA), 7.92-7.80 (d, 2H, BTA), 7.55 (t, 1H, BTA), 7.46 (t, 1H, BTA), 6.62-6.20 (dd, 2H, NH$_2$), 3.83 (dd, 1H, CH), 3.02-2.72 (dd, 2H, CH$_2$). Anal, Calcd for $(C_{16}H_{16}C_{12}N_4OPtS \cdot \frac{1}{2}H_2O)$: C, 28.75; H, 3.92; N, 8.38; S, 4.80. Found: C, 28.57; H, 2.73; N, 8.20; S, 4.67. FABMS: m/z (%) 578.0144 [M+H]$^+$ (100). $^{195}$Pt NMR (DMSO-d$_6$): δ=−2754.

$^1$H NMR (500 MHz, DMSO-d6) of L2Pt: δ=10.50 (s, 1H, NH), 8.76 (s, 1H, Ar—CH), 8.60 (s, 1H, Ar—CH), 8.17-7.78 (m, 6H, BTA), 7.69-7.37 (d, 6H, Ar—CH), 6.95 (t, 1H, BTA), 6.65 (t, 1H, BTA), 4.75 (m, 1H, CH), 4.32 (d, 1H, CH$_2$), 4.15 (d, 1H, CH$_2$), 2.09 (s, 2H, NH$_2$). FTIR: ν (cm-1)=3054 w, 1693 s, 1600 s (C=N), 1532 s, 1437 m, 1302 m. Anal, Calcd for $(C_{30}H_{22}N_4O_3PtS \cdot 4H_2O)$: C, 45.86; H, 3.85; N, 7.13; S, 4.08. Found: C, 45.53; H, 3.42; N, 7.11; S, 6.70. FABMS: m/z (%) 714.1142 [M+H]+(100).

$^1$H NMR (500 MHz, DMSO-d$_6$) of L3Pt: δ=8.17-7.98 (m, 6H, BTA), 7.86 (t, 1H, BTA), 7.82 (t, 1H, BTA), 7.57-7.42 (m, 4H, Pyridine), 5.04 (t, 1H, CH), 4.56-3.98 (m, 2H, CH$_2$). Anal. Calcd for $(C_{22}H_{17}Cl_2N_5OPtS \cdot 2H_2O)$: C, 37.67; H, 3.02; N, 9.98; S, 4.57. Found: C, 38.08; H, 2.72; N, 9.00; S, 3.67. Maldi-tof-MS: m/z 687.2321 [M+Na]$^+$ (100).

Anticancer effects of compounds and complexes according to the present disclosure: L1, L2, L3, L1Pt, L2Pt, and L3Pt To identify the anticancer effect of the compounds L1, L2, and L3 according to Examples 1 to 3 of the present disclosure, and the complexes L1Pt, L2Pt, and L3Pt according to Examples 4 to 6 of the disclosure, the cell viability analysis of cancer cells using CCK-8 was performed on several cancer cell lines (colorectal cancer cell line (HT-29 cell line), breast cancer cell line (MCF-7 and MDA-MB-231), cervical cancer cell line (HeLa cell line), liver cancer cell line (Huh-7 and HepG2), brain glioma cell line (C6), lung cancer cell line (A549), prostate cancer (PC3), kidney cancer (Caki-2), normal liver cell line (AML-12), embryonic kidney cell line (HEK-293), neural stem cell line (NE-4C) and normal breast epithelial cell line (MCF10a)).

CCK-8 (Cell counting kit-8) is analyzed using a highly water-soluble tetrazolium salt-SST-8. [2-(2-methoxy-4-nitrophenyl)-3-(4-nitrophenyl)(2,4-disulfophenyl)-2H-tetrazolium, monosodium salt] is reduced under the presence of an electron medium to produces a water-soluble formazan orange dye. The amount of the formazan dye produced by dehydrogenase in a cell is directly proportional to the number of living cells.

In an experimental method for evaluating the properties of the compounds according to the present disclosure, various cancer cell lines derived from humans and normal cell lines of each tissue derived from humans and mice were used in this experiment. A complete growth medium corresponding to each cell line and having 10% of heat-inactivated FBS added thereto was used to maintain corresponding cells. The maintained cells were suspended in a volume of 200 μl at a density of 1 or 1.5×10$^4$ cells and planted in each well of a 96 well plate. The cells were attached to a 37° C. and 5% CO$_2$ incubator for more than 14 hours, and we waited for a stable state. The next day, we removed the medium from the well. 100 μl of serum-free medium containing drugs of various concentrations (0 (control), 2.5, 5, 10, 20, 30, 40, 50, 100, 200 μM) was added to each well and the cells was cultured therein. On 22 hours after the incubation, 10 μl of CCK-8 solution was added to each well, followed by incubation for 2 hours. A plate on which the culture was completed was measured in terms of absorbance at 450 nm using a microplate reader.

Cell Viability Calculation:
A: Absorbance value measured in a control well
B: Absorbance value measured in a well containing the drug In drawing a graph, the calculated values were graphed using the GraphPad Prism application. The statistical significance of the numerical values was identified via One-way ANOVA with Dunnett's multiple comparison test. * $p<0.05$  $p<0.01$, * $p<0.001$ vs. control indicate the significance.

The cancer cells viability analysis results using CCK-8 on colorectal cancer cell line (HT-29), breast cancer cell line (MCF-7 and MDA-MB-231), cervical cancer cell line (HeLa), liver cancer cell line (Huh-7 and HepG2), brain glioma cell line (C6)), lung cancer cell line (A549), prostate cancer cell line (PC3) and renal cancer cell line (Caki-2) as treated with the compounds according to Examples 1 to 3 of the present disclosure and the complexes according to Examples 4 to 6 and cisplatin and BTA as the controls are shown below.

In Table 1 below, each compound was applied to the cells at 0, 2.5, 5, 10, 20, 30, 40, 50, 100, and 200 μM, and the cells was cultured in a medium free of serum for 24 hours. The measured absorbance value was converted to a % value based on a value of 0, such that a IC$_{50}$ value was calculated. Each experiment was performed 2 to 3 times and a standard deviation value was obtained.

TABLE 1

| IC$_{50}$ (μM) | HT-29 (colorectal cancer) | MCF-7 (breast cancer) | MDA-MB-231 (breast cancer) | MCF10a (Normal breast) | HeLa (cervical cancer) | Huh-7 (liver cancer) | HepG2 (liver cancer) |
|---|---|---|---|---|---|---|---|
| Cisplatin | 39.07 ± 0.61 | 203.8 ± 27.32 | 181.05 ± 48.68 | 95.95 ± 6.72 | 26.23 ± 5.61 | 38.65 ± 18.48 | 54.25 ± 31.81 |
| BTA | 275.3 ± 5.03 | 103.99 ± 28.57 | >500 | 401.4 ± 136.32 | 76.41 ± 23.44 | 406.03 ± 35.67 | 52.00 ± 5.715 |

TABLE 1-continued

| | | | | | | | |
|---|---|---|---|---|---|---|---|
| L1 | 29.86 ± 0.27 | 65.94 ± 12.34 | 62.02 ± 6.5 | 65.13 ± 1.88 | 41.91 ± 3.375 | 69.13 ± 5.25 | 5.94 ± 0.501 |
| L1Pt | 42.64 ± 5.61 | 59.03 ± 11.06 | 80.79 ± 10.48 | 46.91 ± 5.14 | 64.75 ± 0.31 | 69.36 ± 1.24 | 7.49 ± 0.159 |
| L2 | 135 ± 4.41 | 98.15 ± 7.92 | 151.85 ± 19.85 | 79.3 ± 25.4 | 47.08 ± 6.065 | 95.93 ± 15.04 | 14.21 ± 7.059 |
| L2Pt | 172.65 ± 3.23 | >500 | >500 | >500 | 221 ± 15.8 | 197.15 ± 3.75 | 31.59 ± 3.62 |
| L3 | 70.5 ± 0.29 | 190.35 ± 16.55 | >500 | >500 | 98.96 ± 3.54 | 177.8 ± 2.6 | >500 |
| L3Pt | >500 | >500 | >500 | >500 | >500 | 172.77 ± 24.29 | >500 |

| $IC_{50}$ (μM) | AML12 (Normal liver) | C6 (brain glioma) | NC-4C (Neural stem cell) | A549 (lung cancer) | PC3 (prostate cancer) | Caki-2 (kidney cancer) | HEK293 (embryonic kidney) |
|---|---|---|---|---|---|---|---|
| Cisplatin | 32.09 ± 4.45 | 226.57 ± 34.28 | 9.005 ± 0.28 | >500 | >500 | >500 | 65.46 ± 4.06 |
| BTA | >500 | 424.73 ± 47.75 | 60.93 ± 2.93 | >500 | 181.67 ± 7.79 | 462.8 ± 44.1 | >500 |
| L1 | 137.65 ± 24.15 | 77.84 ± 9.73 | 36.82 ± 3.66 | 100.16 ± 8.44 | 94.99 ± 0.82 | 75.65 ± 3.44 | 68.15 ± 2.79 |
| L1Pt | 139.05 ± 0.85 | 93.32 ± 22.74 | 25.72 ± 1.66 | 167.2 ± 11.2 | 55.72 ± 7.47 | 105.66 ± 8.54 | 54.87 ± 2.83 |
| L2 | >500 | 143.23 ± 32.74 | 28.23 ± 0.06 | 182.45 ± 0.85 | 116.3 ± 5.05 | 159 ± 4.3 | 138.9 ± 20.1 |
| L2Pt | >500 | >500 | 47.02 ± 4.12 | >500 | >500 | >500 | 211.5 ± 14.9 |
| L3 | >500 | 142.45 ± 15.35 | 22.45 ± 2.44 | >500 | 130.25 ± 34.72 | >500 | >500 |
| L3Pt | >500 | >500 | 32.44 ± 6.02 | >500 | >500 | >500 | 205.95 ± 7.45 |

Further, FIGS. 3a to 3e show a graph in which a $IC_{50}$ value which is obtained based on 2 to 3 times executions of the cell viability analysis is converted to a Log $IC_{50}$ value. In statistical analysis, comparative reliability values for cisplatin via the One-way ANOVA Dunnett test were expressed as * p<0.5,  p<0.01, * p<0.001. The comparative reliability values for BTA were expressed as #p<0.5, ##p<0.01, and ## #p<0.001. A red line represents the value of cisplatin. A blue line represents the value of BTA.

As may be seen from FIGS. 3a to 3e, cisplatin did not have a great effect on lung cancer, prostate cancer, and kidney cancer. BTA did not have greater effect on colorectal cancer, brain glioma, and lung cancer.

However, L1 and L1Pt according to the present disclosure exhibited a greater toxic effect against cancer cell lines of colorectal cancer, breast cancer, liver cancer, brain glioma, lung cancer, prostate cancer, and kidney cancer than the cisplatin and BTA did. In particular, it could be identified that the L1 and L1Pt according to the present disclosure exhibited superior effects on breast cancer, liver cancer, brain glioma, lung cancer, prostate cancer, and kidney cancer than the rest of the compounds did.

Further, L2 according to the present disclosure had a greater toxic effect on cancer cell lines on lung cancer, prostate cancer, and kidney cancer than cisplatin did. L2 exhibited greater cell toxicity against colorectal cancer, breast cancer, liver cancer, brain glioma, lung cancer, prostate cancer, and kidney cancer than BTA did. Further, it could be identified that L2Pt exhibited greater cell toxicity on colorectal cancer than BTA did.

L3 according to the present disclosure had greater cell toxicity on prostate cancer and kidney cancer than cisplatin did, and had greater cell toxicity on colorectal cancer breast cancer and brain glioma than BTA did. It could be identified that L3Pt only exerts cell toxicity effects on liver cancer.

FIG. 4 shows a graph in which a $IC_{50}$ value which is obtained based on 2 to 3 times executions of the cell viability analysis is converted to a Log $IC_{50}$ value. In statistical analysis, comparative reliability values for cisplatin via the One-way ANOVA Dunnett test were expressed as *** p<0.001. The comparative reliability values for BTA were expressed as #p<0.5. A red line represents the value of cisplatin. A blue line represents the value of BTA.

While cisplatin had the strong toxicity against normal hepatocytes (AML12), L1 and L1Pt according to the present disclosure exhibited the cytotoxicity decrease by more than 10 times. It could be identified that L2, L2Pt, L3, and L3Pt did not exhibit liver cytotoxicity.

L1, L1Pt and L2 according to the present disclosure had weak cytotoxicity against breast epithelial cells (MCF10a). However, statistically, there was no significant difference between L1, L1Pt and L2 and cisplatin and BTA in terms of cytotoxicity. L2Pt, L3, and L3Pt exhibited weaker cytotoxicity or no cytotoxicity than cisplatin and BTA did.

It was identified that while cisplatin had toxicity against brain neurons (NE-4C) at a very low concentration of cisplatin, all of L1, L1Pt, L2, L2Pt, L3, and L3Pt according to the present disclosure had greater toxicity than BTA did, but had decrease in toxicity by 2 to 5 times than cisplatin did.

All of L1, L1Pt, L2, L2Pt, L3, and L3Pt had toxicity on normal kidney cells (HEK-293) similar or weaker than that of cisplatin.

FIGS. 5a to 5b show results of comparing and analyzing effects of each of the compounds according to the present disclosure and cisplatin and BTA as controls in various cancer cell lines and normal cells.

In the above description, the present disclosure was described with reference to the preferred embodiments according to the present disclosure. However, those skilled in the art will appreciate that various modifications and changes may be made to the present disclosure without departing from the spirit and scope of the present disclosure as described in the following claims.

What is claimed is:

1. A compound having a structure represented by the following Chemical Formula 1:

[Chemical Formula 1]

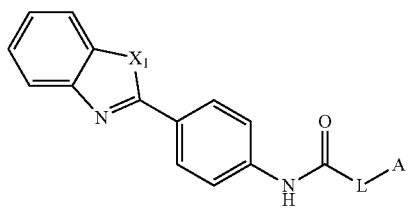

wherein in the Chemical Formula 1, $X_1$ represents NH, O or S, wherein L represents

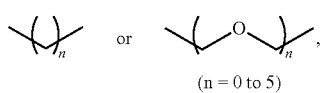

(n = 0 to 5)

wherein A represents one of the following Chemical Formulas A-1 to A-3:

[Chemical Formula A-1]

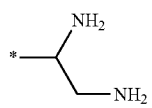

[Chemical Formula A-2]

[Chemical Formula A-3]

wherein in the Chemical Formula A-2, each of $R_1$ to $R_8$ independently represents H, $OCH_3$ or F, wherein in the Chemical Formula A-3, $X_2$ represents NH, O or S.

2. The compound of claim 1, wherein the compound has a structure represented by one of following Chemical Formulas 1-1 to 1-3:

[Chemical Formula 1-1]

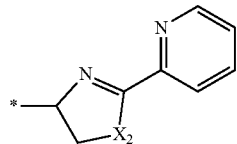

[Chemical Formula 1-2]

[Chemical Formula 1-3]

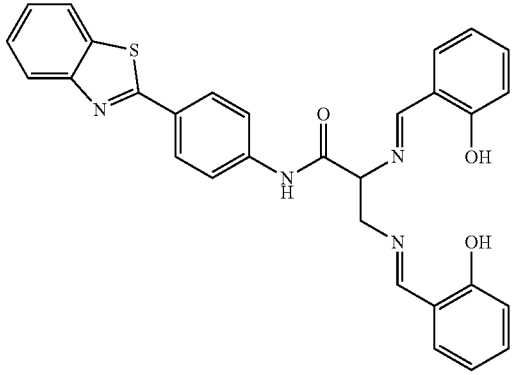

3. A pharmaceutical composition containing the compound of claim 1 at an effective amount and further containing a pharmaceutically acceptable carrier, wherein the composition has anticancer activity on cancer cells.

4. The pharmaceutical composition of claim 3, wherein the composition targets cancer cells of at least one selected from a group consisting of colorectal cancer, breast cancer, liver cancer, brain glioma, lung cancer, prostate cancer, kidney cancer and cervical cancer, and has anticancer activity on the cancer cells.

5. The pharmaceutical composition of claim 3, wherein when the compound has a structure of Chemical Formula 1-1

[Chemical Formula 1-1]

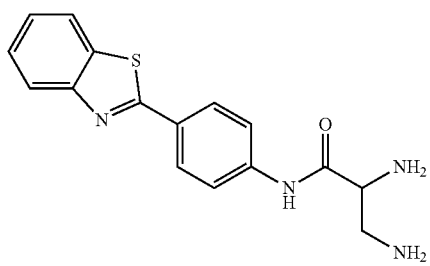

the composition has anticancer activity against colorectal cancer, breast cancer, liver cancer, brain glioma, lung cancer, prostate cancer or kidney cancer.

6. The pharmaceutical composition of claim 3, wherein when the compound has a structure of Chemical Formula 1-2

[Chemical Formula 1-2]

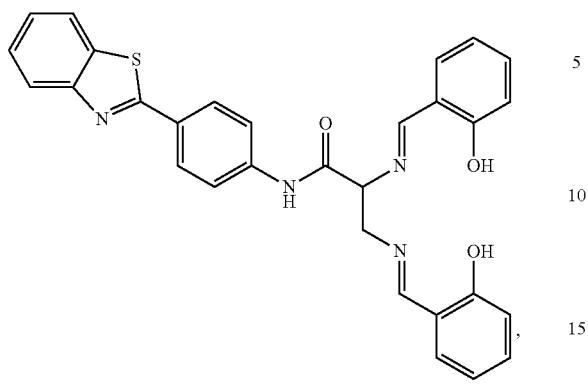

the composition has anticancer activity against colorectal cancer, breast cancer, liver cancer, brain glioma, lung cancer, prostate cancer or kidney cancer.

7. The pharmaceutical composition of claim 3, wherein when the compound has a structure of Chemical Formula 1-3

[Chemical Formula 1-3]

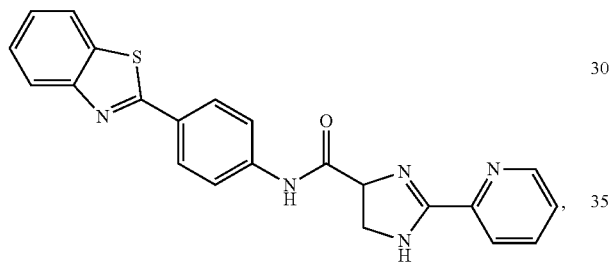

the composition has anticancer activity against colorectal cancer, breast cancer, brain glioma, prostate cancer or kidney cancer.

8. A complex containing a compound having a structure represented by a following Chemical Formula 1 as a ligand, and a metal atom coordinated to the ligand:

[Chemical Formula 1]

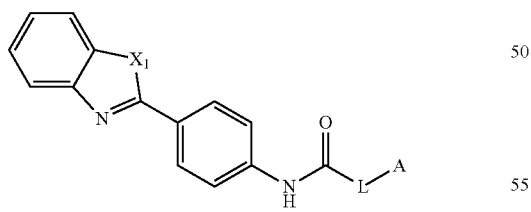

wherein in the Chemical Formula 1, $X_1$ represents NH, O or S, wherein L represents

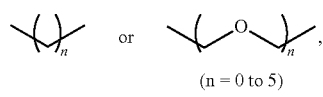

(n = 0 to 5)

wherein A represents one of following Chemical Formulas A-1 to A-3:

[Chemical Formula A-1]

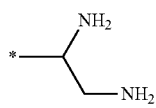

[Chemical Formula A-2]

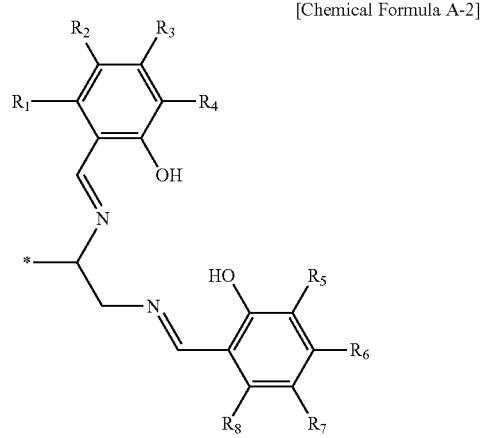

[Chemical Formula A-3]

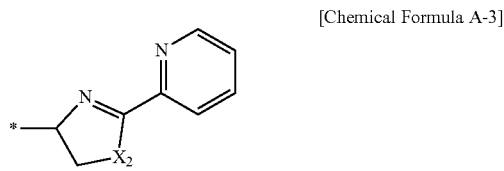

wherein in the Chemical Formula A-2, each of $R_1$ to $R_8$ independently represents H, $OCH_3$ or F, wherein in the Chemical Formula A-3, $X_2$ represents NH, O or S.

9. The complex of claim 8, wherein the metal atom is platinum (Pt).

10. The complex of claim 8, wherein the complex has a structure represented by one of following Chemical Formulas 3-1 to 3-3:

[Chemical Formula 3-1]

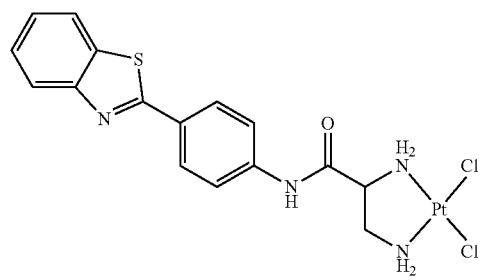

-continued

[Chemical Formula 3-2]

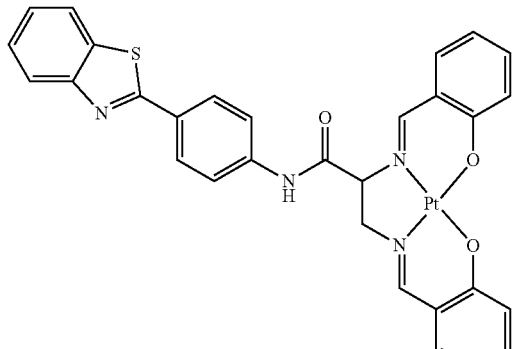

[Chemical Formula 3-3]

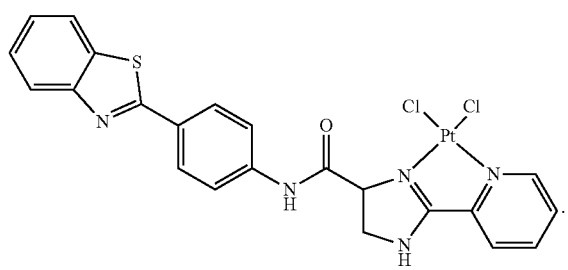

11. A pharmaceutical composition containing the complex of claim 8 at an effective amount and further containing a pharmaceutically acceptable carrier, wherein the composition has anticancer activity on cancer cells.

12. The pharmaceutical composition of claim 11, wherein the composition targets cancer cells of at least one selected from a group consisting of colorectal cancer, breast cancer, liver cancer, brain glioma, lung cancer, prostate cancer, kidney cancer and cervical cancer, and has anticancer activity on the cancer cells.

13. The pharmaceutical composition of claim 11, wherein when the complex has a structure represented by Chemical Formula 3-1

[Chemical Formula 3-1]

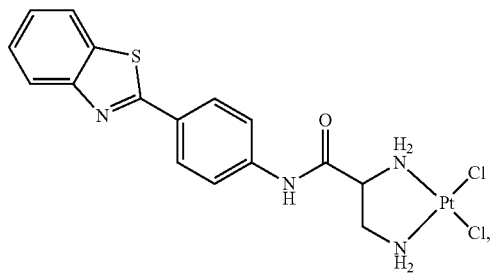

the composition has anticancer activity against colorectal cancer, breast cancer, liver cancer, brain glioma, lung cancer, prostate cancer or kidney cancer.

14. The pharmaceutical composition of claim 11, wherein when the complex has a structure represented by Chemical Formula 3-2

[Chemical Formula 3-2]

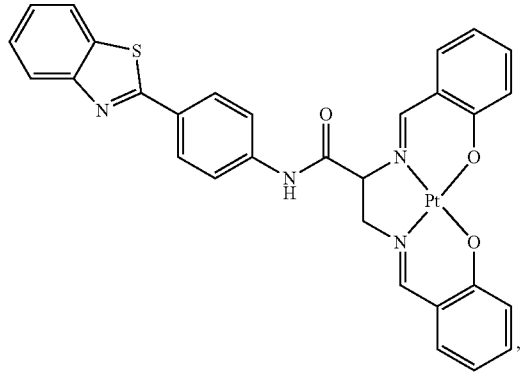

the composition has anticancer activity against colorectal cancer.

15. The pharmaceutical composition of claim 11, wherein when the complex has a structure represented by Chemical Formula 3-3

[Chemical Formula 3-3]

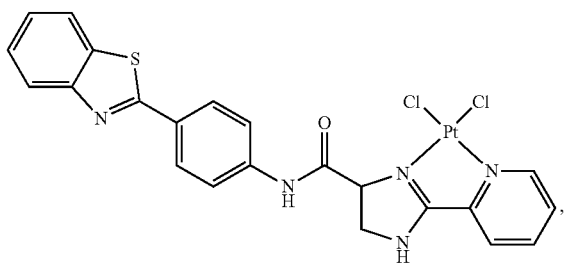

the composition has anticancer activity against liver cancer.

16. An anticancer drug containing, as an active ingredient, the compound of claim 1.

17. An anticancer drug containing, as an active ingredient, the complex of claim 8.

18. An anticancer drug containing, as an active ingredient, the pharmaceutical composition of claim 3.

19. An anticancer drug containing, as an active ingredient, the pharmaceutical composition of claim 11.

* * * * *